(12) United States Patent
Suzuki et al.

(10) Patent No.: US 9,168,003 B2
(45) Date of Patent: Oct. 27, 2015

(54) IMAGING APPARATUS FOR DIAGNOSIS AND CONTROL METHOD THEREOF

(75) Inventors: Hironobu Suzuki, Fujinomiya (JP); Junya Furuichi, Isehara (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 13 days.

(21) Appl. No.: 13/436,754

(22) Filed: Mar. 30, 2012

(65) Prior Publication Data

US 2012/0215091 A1      Aug. 23, 2012

Related U.S. Application Data

(63) Continuation of application No. PCT/JP2010/005770, filed on Sep. 24, 2010.

(30) Foreign Application Priority Data

Sep. 30, 2009   (JP) .................................. 2009-227838
Sep. 30, 2009   (JP) .................................. 2009-227839

(51) Int. Cl.
*A61B 8/12*          (2006.01)
*A61B 5/00*          (2006.01)
(Continued)

(52) U.S. Cl.
CPC .............. *A61B 5/6852* (2013.01); *A61B 5/0066* (2013.01); *A61B 8/12* (2013.01);
(Continued)

(58) Field of Classification Search
CPC ...... A61B 5/6852; A61B 5/0066; A61B 8/12; A61B 8/4245; A61B 8/4461; A61B 8/466; A61B 8/483; A61B 8/5207

USPC ........... 600/407, 473, 475–478; 356/345, 346
See application file for complete search history.

(56) References Cited

U.S. PATENT DOCUMENTS 5,107,844 A      4/1992 Kami et al.
5,830,145 A *   11/1998 Tenhoff ....................... 600/463
(Continued)

FOREIGN PATENT DOCUMENTS

EP     1 839 569 A2     10/2007
JP     2-271844 A       11/1990
(Continued)

OTHER PUBLICATIONS

International Search Report (PCT/ISA/210) issued on Dec. 21, 2010, by Japanese Patent Office as the International Searching Authority for International Application No. PCT/JP2010/005770.

*Primary Examiner* — Elmer Chao
(74) *Attorney, Agent, or Firm* — Buchana Ingersoll & Rooney PC

(57) ABSTRACT

An imaging apparatus for diagnosis and associated control method constructs multiple cross-sectional images in an axial direction inside the body lumen based on line data generated by radially operating a transmitting and receiving unit, and includes a receiving mechanism which receives a count value from a reference position of the transmitting and receiving unit, storage for storing the count value and the line data correlated with each other, an arrangement for constructing a longitudinal-sectional image by aligning the line data based on the count value, a display which displays the longitudinal-sectional image; and a mechanism which reads out line data correlated with the same count value as that of the line data disposed at the position appointed by the user on the displayed longitudinal-sectional image and reconstructing the cross-sectional image.

7 Claims, 13 Drawing Sheets

(51) Int. Cl.
*A61B 8/00* (2006.01)
*A61B 8/08* (2006.01)

(52) U.S. Cl.
CPC ............ *A61B 8/4245* (2013.01); *A61B 8/4461* (2013.01); *A61B 8/466* (2013.01); *A61B 8/483* (2013.01); *A61B 8/5207* (2013.01)

(56) References Cited

U.S. PATENT DOCUMENTS

| | | | |
|---|---|---|---|
| 5,921,926 A * | 7/1999 | Rolland et al. | 600/407 |
| 6,807,292 B1 | 10/2004 | Goto et al. | |
| 2006/0241469 A1* | 10/2006 | Rold et al. | 600/459 |
| 2007/0232891 A1 | 10/2007 | Hirota | |
| 2007/0232892 A1* | 10/2007 | Hirota | 600/407 |
| 2009/0076445 A1* | 3/2009 | Furnish | 604/95.01 |

FOREIGN PATENT DOCUMENTS

| | | |
|---|---|---|
| JP | 5-095949 A | 4/1993 |
| JP | 10-262964 A | 10/1998 |
| JP | 11-318884 A | 11/1999 |
| JP | 2001-017430 A | 1/2001 |
| JP | 2001-079007 A | 3/2001 |
| JP | 2004-298352 A | 10/2004 |
| JP | 2007-267867 A | 10/2007 |
| WO | WO 99/46733 A1 | 9/1999 |

* cited by examiner

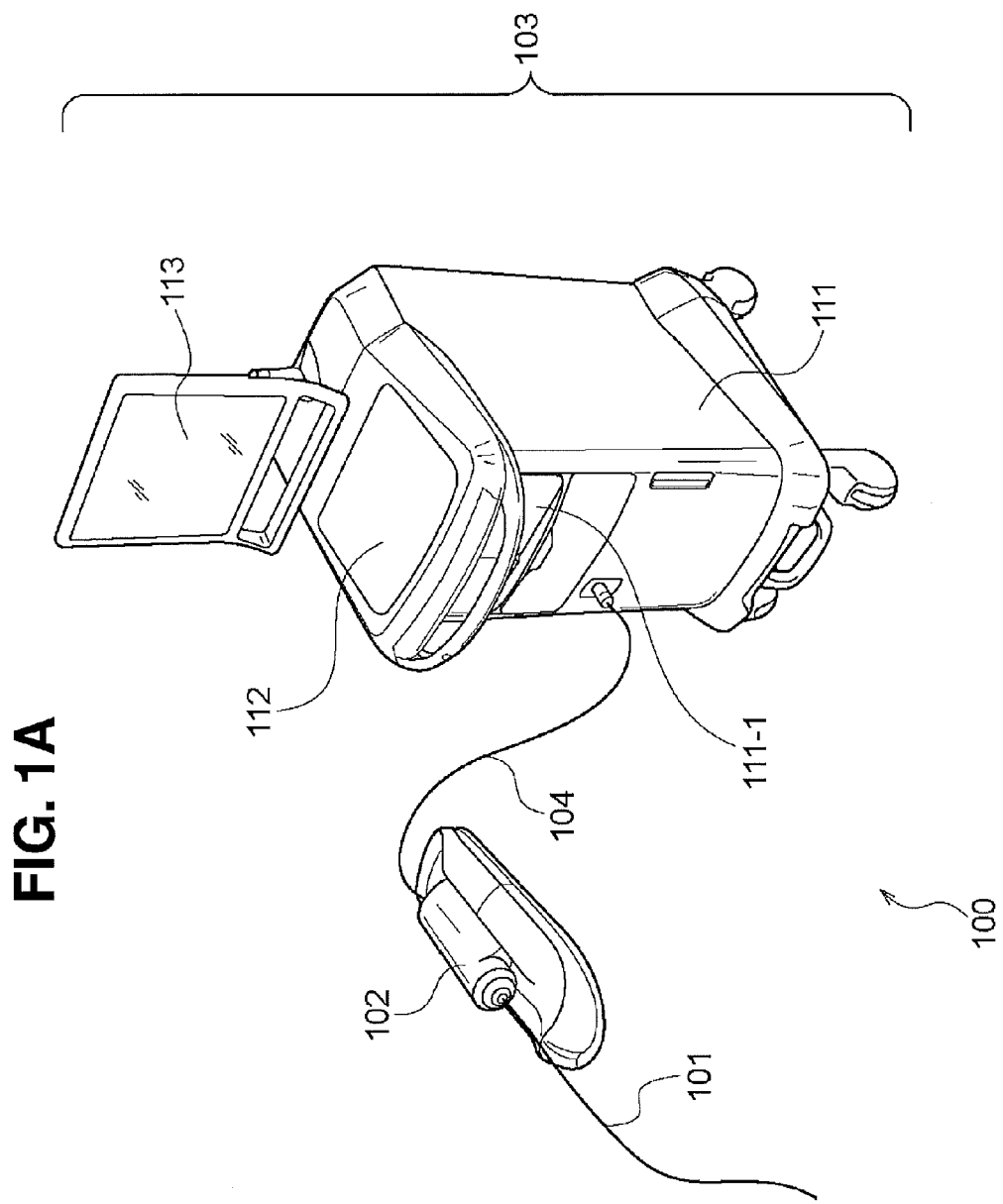

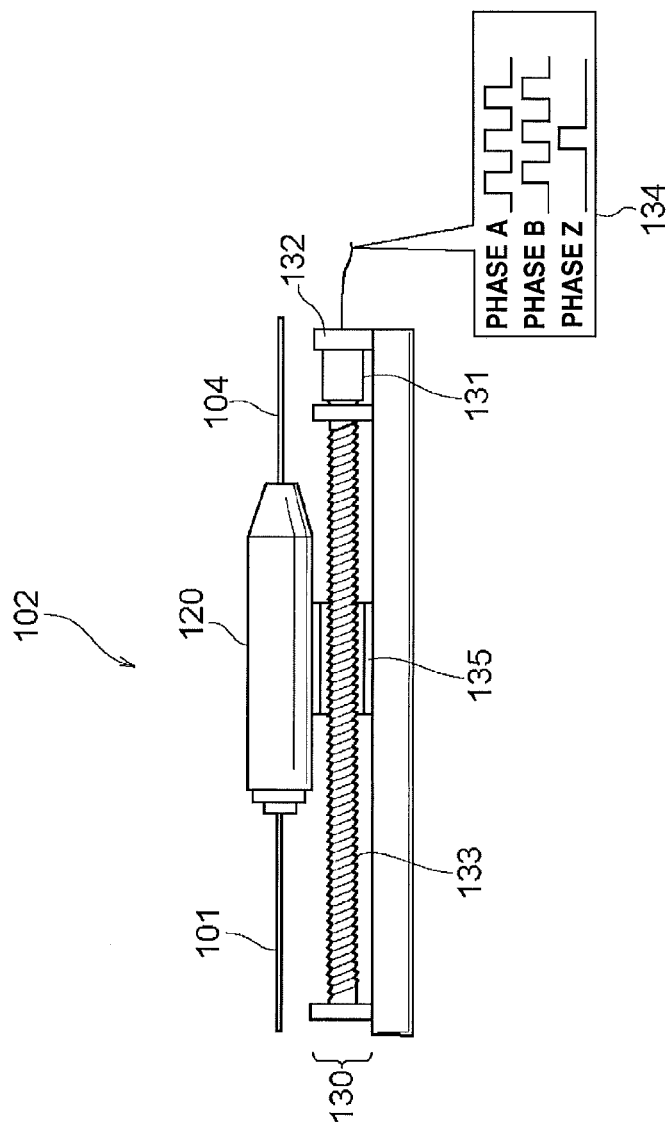

| NO. | LINE DATA FILE IDENTIFIER | COUNT VALUE |
|---|---|---|
| 1 | DataFile0001 | 150 |
| 2 | DataFile0002 | 200 |
| 3 | DataFile0003 | 250 |
| 4 | DataFile0004 | 300 |
| 5 | DataFile0005 | 330 |
| 6 | DataFile0006 | 400 |

⋮

| N-2 | DataFile000N-2 | 770 |
|---|---|---|
| N-1 | DataFile000N-1 | 830 |
| N | DataFile000N | 900 |

IMAGING APPARATUS FOR DIAGNOSIS AND CONTROL METHOD THEREOF

This application is a continuation of International Application No. PCT/JP2010/0005770 filed on Sep. 2, 2010, and claims priority to Japanese Application No. 2009-227838 filed on Sep. 30, 2009 and Japanese Application No. 2009-227839 filed on Sep. 30, 2009, the entire content of all three of which is incorporated herein by reference.

TECHNICAL FIELD

The present invention generally relates to an imaging apparatus for diagnosis and a control method thereof.

BACKGROUND DISCUSSION

In the past, an imaging apparatus for diagnosis has been used for diagnosis of arteriosclerosis, for diagnosis before an operation or medical procedure, at the time of an endovascular treatment by a high functional catheter such as a balloon catheter, a stent and the like or to confirm results after an operation or medical procedure.

An example of a representative imaging apparatus for diagnosis is an intravascular ultrasound (IVUS) apparatus for diagnosis. Generally, the intravascular ultrasound apparatus for diagnosis is an apparatus which emanates an ultrasound wave inside a blood vessel while rotating a transmitting and receiving unit in a state of inserting an ultrasound probe unit installed with the transmitting and receiving unit composed of an ultrasound vibrator inside a blood vessel, which carries out a radial scan by receiving a reflection wave from the living body and which visualizes a cross-sectional image of a blood vessel based on the intensity of an ultrasound echo signal generated by applying a process of amplification, detection or the like.

An example of another imaging apparatus for diagnosis is an optical coherent tomography (OCT) apparatus for diagnosis which carries out diagnosis by utilizing coherency of light. An example is disclosed in Japanese unexamined Patent Publication No. 2001-79007.

The optical coherent tomography apparatus for diagnosis is an apparatus in which measurement light is emitted inside a blood vessel while rotating a transmitting and receiving unit in a state of inserting an optical probe unit which is built-in with a transmitting and receiving unit mounted with an optical lens and an optical mirror at the distal end and an optical fiber inside the blood vessel, a radial scan is carried out by light-receiving reflected light from a biological tissue, and a cross-sectional image of the blood vessel based on interference light is visualized by making the reflected light obtained depending on this and a reference light split from the measurement light beforehand interfere each other.

Further, recently, as an improved version of the optical coherent tomography apparatus for diagnosis, there has been developed an optical frequency domain imaging (OFDI) apparatus for diagnosis utilizing wavelength sweep.

With respect to the optical frequency domain imaging (OFDI) apparatus for diagnosis utilizing wavelength sweep, the basic constitution thereof is similar as that of the optical coherent tomography (OCT) apparatus for diagnosis, but there exists a feature in an aspect that a light source having a longer wavelength compared with the optical coherent tomography (OCT) apparatus for diagnosis is used and also, light having different wavelengths is emitted continuously. Then, a mechanism for variably changing the optical path length of the reference light is made unnecessary by employing a construction in which reflected-light intensity at each point in the depth direction of the biological tissue is found out by frequency analysis of the interference light.

It should be noted in this description hereinafter that the intravascular ultrasound (IVUS) apparatus for diagnosis, the optical coherent tomography (OCT) apparatus for diagnosis and the optical frequency domain imaging (OFDI) apparatus for diagnosis utilizing wavelength sweep are named generically and to be referred to as an "imaging apparatus for diagnosis".

Generally, the multiple cross-sectional images visualized by using such an imaging apparatus for diagnosis are displayed on a display apparatus in real time during the radial operation of the transmitting and receiving unit. Also, the multiple cross-sectional images displayed on the display apparatus (or line data used for visualizing the cross-sectional images) are stored concurrently in a predetermined memory and if required, the system allows them to be redisplayed on the display apparatus as many times as requested.

However, in an imaging apparatus for diagnosis known up until now, the apparatus was constructed so that multiple cross-sectional images (or line data) which are visualized during an interval from the start of the radial operation to the termination thereof are stored at a predetermined position inside the memory re-displayably in sequence regardless of the presence or absence of variation in operation speed of the radial operation of the transmitting and receiving unit (specifically, axial direction motion speed along the blood vessel).

Consequently, in case of redisplaying the multiple cross-sectional images on the display apparatus, there used to be employed a constitution in which the respective cross-sectional images are to be displayed without regard to the position in the actual axial direction. In other words, the redisplayed cross-sectional image did not make it possible for a user to accurately grasp the cross-sectional image as to which position the transmitting and receiving unit actually moved to in the axial direction of the blood vessel after the radial operation was started.

Consequently, for example, even in a case in which visualization of a detailed cross-sectional image is demanded by carrying out a radial operation and thereafter, by presuming a disorder region based on the re-displayed cross-sectional image and by carrying out again a radial operation at the position of the presumed disorder region, it is not possible for the user to comprehend the accurate position of aforesaid disorder region and there was a problem that it was not possible to move transmitting and receiving unit to aforesaid position accurately.

SUMMARY

The imaging apparatus for diagnosis and control method disclosed here were developed to make it possible for the user, on an occasion when redisplaying multiple visualized cross-sectional images in an imaging apparatus for diagnosis, to accurately and also relatively easily recognize which positions in the axial direction the cross-sectional images belong to.

The imaging apparatus for diagnosis and method reduce an inspection load on a patient and improve usability of a user such that further details can be re-observed by easily searching the position of the blood vessel region observing an image of a lesion portion, disorder portion or the like, which the user is interested in, among multiple visualized cross-sectional images, and by moving the sensor portion of the catheter.

An imaging apparatus for diagnosis is provided with a constitution such as follows in order to achieve the object mentioned above. More specifically, an imaging apparatus for diagnosis which constructs multiple cross-sectional images in an axial direction inside a body lumen (e.g., blood vessel) includes; a transmitting and receiving unit carrying out signal transmission and reception continuously and receiving a reflected signal from the inside of the body lumen while moving in the axial direction inside the body lumen; and receiving means receiving information relating to an moving amount in the axial direction from a predetermined reference position of the transmitting and receiving unit. The multiple cross-sectional images are constructed based on the received reflected signal or line data generated from the reflected signal, the respective line data or the respective cross-sectional images are correlated with information relating to the moving amount in the axial direction from the predetermined reference position of the transmitting and receiving unit, which is received when the respective cross-sectional images are constructed.

According to the disclosure here, on an occasion when redisplaying visualized multiple cross-sectional images in an imaging apparatus for diagnosis, it becomes possible for a user to recognize accurately and also relatively easily the axial direction position associated with the cross-sectional image.

Also, it is possible to move the transmitting and receiving unit accurately to a position in the axial direction in response to an appointed content which is appointed by a user on the displayed image.

According to another aspect, an imaging apparatus for diagnosis comprises: a transmitting and receiving unit configured to be positioned in and axially moved along a living body lumen and to carry out signal transmission and reception; a signal processing unit operatively connected to the transmitting and receiving unit, the signal processing unit being configured to obtain reflected signals reflected from inside the body lumen, and to construct multiple cross-sectional images of the inside of the body lumen in an axial direction based on the obtained reflected signal; and splay apparatus operatively connected to the signal processing unit, the display apparatus being configured to display the cross-sectional images constructed by the signal processing unit. The signal processing unit comprises: receiving means for receiving information relating to a moving amount in the axial direction from a predetermined reference position of the transmitting and receiving unit; storage means for storing respective ones of the constructed multiple cross-sectional images in a manner correlated with information relating to moving amounts in the axial direction from the predetermined reference position of the transmitting and receiving unit, which is received when the respective ones of the multiple cross-sectional images are constructed; construction means for constructing a longitudinal-sectional image based on data of the multiple cross-sectional image stored in the storage means, with the constructed longitudinal-sectional image being displayable on the display apparatus; and readout means for identifying a user-identified position on the displayed longitudinal-sectional image and concurrently, read out, from the storage means, the cross-sectional image which is disposed at the identified position. The display means displays the read out cross-sectional image.

Another aspect of the disclosure here involves an imaging apparatus for diagnosis which obtains a reflected signal from inside a body lumen while a transmitting and receiving unit continuously carrying out signal transmission and reception is moved in an axial direction inside the body lumen, to generate line data used for constructing a cross-sectional image of the inside of the body lumen based on the obtained reflected signal, and which concurrently constructs multiple cross-sectional images in an axial direction inside the body lumen by using the generated line data. The imaging apparatus comprises: receiving means for receiving information relating to a moving amount in the axial direction from a predetermined reference position of the transmitting and receiving unit; storage means for storing the information relating to the moving amount in the axial direction from the predetermined reference position of the transmitting and receiving unit; construction means for constructing a longitudinal-sectional image with respect to the multiple cross-sectional images constructed in the axial direction by extracting line data corresponding to predetermined coordinate positions in the respective cross-sectional images from among the multiple line data used for constructing the respective cross-sectional images, concurrently, by obtaining information relating to a moving amount of the transmitting and receiving unit in the axial direction from the predetermined reference position, which is received when the extracted line data is generated, and by aligning the extracted line data at a position in response to the information relating to the obtained moving amount; display means for displaying the constructed longitudinal-sectional image; and reconstruction means for reconstructing the cross-sectional image by identifying the line data disposed at a user-identified position on the displayed longitudinal-sectional image, concurrently, by reading out, from the storage means, line data with which there is correlated the same information as the information relating to the moving amount in the axial direction stored by being correlated with the line data, and by using the read out line data. The display means is configured to display the reconstructed cross-sectional image together with the longitudinal-sectional image.

Other features and advantages will become clear according to the following explanations with reference to the attached drawings. In the attached drawings, identical reference numbers identify identical or similar features.

BRIEF DESCRIPTION OF DRAWINGS

The attached drawings are included in the specification, constitute a portion thereof, show embodiments disclosed as examples, and together with the following detailed description explaining principles, features and aspects of the imaging apparatus for diagnosis and control method disclosed here.

FIG. 1A is a diagram showing an outward-appearance constitution of an imaging apparatus for diagnosis;

FIG. 1B is a view showing a detailed constitution of a scanner & pull-back unit;

DETAILED DESCRIPTION

Figure 2:
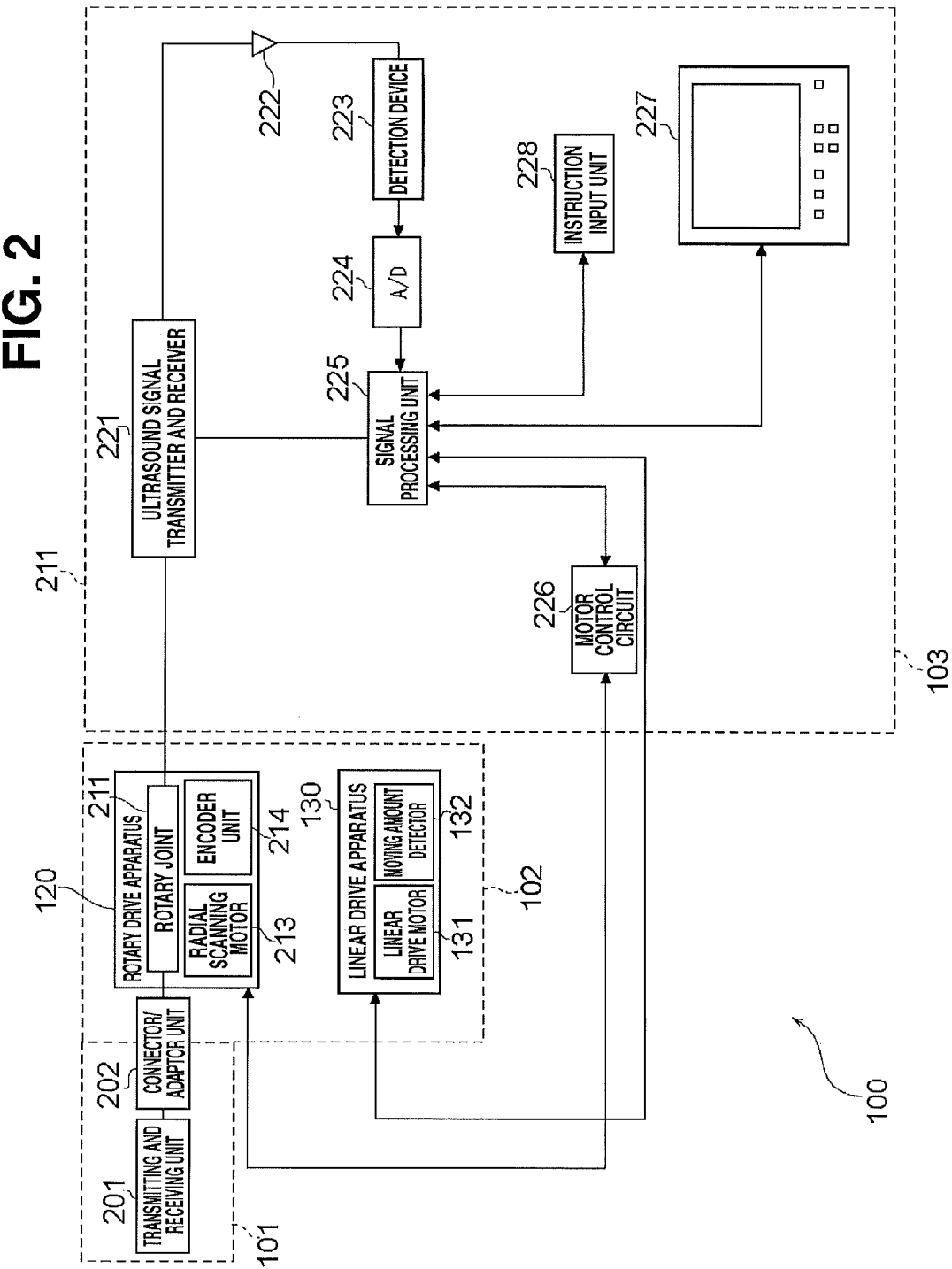
FIG. 2 is a diagram showing a functional constitution of an intravascular ultrasound apparatus for diagnosis.

Set forth below is a detailed description of the imaging apparatus for diagnosis and control method disclosed here, referring to the drawings which illustrates several embodiments described by way of example.

First Embodiment

1. Outward-Appearance Construction of Imaging Apparatus for Diagnosis

FIG. 1A a diagram showing the outward-appearance of the overall imaging apparatus for diagnosis (intravascular ultrasound (IVUS) apparatus for diagnosis, optical coherent tomography (OCT) apparatus or optical frequency domain imaging (OFDI) apparatus for diagnosis utilizing wavelength sweep) 100 relating to one embodiment disclosed by way of example.

As shown in FIG. 1A, the imaging apparatus for diagnosis 100 includes a probe unit 101, a scanner & pull-back unit 102 and an operation control apparatus 103. The scanner & pull-back unit 102 and the operation control apparatus 103 are connected by a signal line 104.

The probe unit 101 is inserted directly into the interior of a blood vessel (inside of a body lumen or body cavity) and the state or condition inside the blood vessel is measured using a transmitting and receiving unit. The scanner & pull-back unit 102 is removable with respect to the probe unit 101 in which a motor is built-in, and radial operation of the transmitting and receiving unit inside the probe unit 101 is defined.

The operation control apparatus 103 is configured to permit, when drawing-out a cross-sectional image inside a blood vessel, the input of various kinds of set values, and to process data obtained by measurement and for displaying the data as a processed result in the form of a cross-sectional image or the like.

In the operation control apparatus 103, a reference numeral 111 indicates a main body control unit which, for example, processes data obtained by measurement and outputs the processed result. A reference numeral 111-1 indicates a printer & DVD recorder which, for example, prints the processed result in the main body control unit 111 and stores the result as stored data.

A reference numeral 112 indicates an operation panel allowing a user to input various kinds of set values through the operation panel 112. A reference numeral 113 indicates an LCD monitor as a display apparatus which displays, for example, a processed result in the main body control unit 111.

2. Detailed Construction of Scanner & Pull-Back Unit

FIG. 1B illustrates details of the scanner & pull-back unit 102. The scanner & pull-back unit 102 is provided with a rotary drive apparatus 120 and a linear drive apparatus 130, which define the radial operation of the transmitting and receiving unit inside the probe unit 101.

The rotary drive apparatus 120 plays a role in defining the rotation (rotational operation) of the transmitting and receiving unit inside the probe unit 101 in the circumferential direction. The rotational operation is realized by the driving operation of a radial scanning motor.

The linear drive apparatus 130 plays a role in defining the movement (axial direction motion) of the transmitting and receiving unit inside the probe unit 101 in the axial direction (the distal direction in body lumen and the opposite direction thereto). The axial direction motion is realized by driving a linear drive motor 131, rotating a ball screw 133 and operating a supporting portion 135 which supports the rotary drive apparatus 120 in the linear direction.

The linear drive apparatus 130 is provided with a moving amount detector 132 for detecting an operation of the linear drive motor 131 and calculating the moving amount of the rotary drive apparatus 120 from a predetermined reference position in the axial direction. In this embodiment disclosed by way of example, as the moving amount detector 132, a three-phase encoder is used. Reference numeral 134 is one example of pulse signals in phase A, phase B and phase Z outputted from the three-phase encoder.

In the operation control apparatus 103, by counting the pulse number of the pulse signal 134 outputted from the moving amount detector 132 and concurrently by detecting a phase, the moving amount of the rotary drive apparatus 120 in the axial direction and the moving direction thereof are judged.

3. Operational and Functional Features of Intravascular Ultrasound Apparatus for Diagnosis The description which follows describes, with reference to FIG. 2, main functional or operational features of the intravascular ultrasound apparatus for diagnosis (IVUS) relating to this embodiment disclosed by way of example. FIG. 2 schematically illustrates the intravascular ultrasound apparatus for diagnosis 100 shown in FIG. 1A. The intravascular ultrasound apparatus for diagnosis 100 includes a probe unit 101, a scanner & pull-back unit 102 and an operation control apparatus 103.

The probe unit 101 includes a transmitting and receiving unit 201 composed of an ultrasound vibrator inside the distal end, and in a state in which the probe unit 101 is inserted into the blood vessel inside, the transmitting and receiving unit 201 transmits an ultrasound wave in the cross-sectional direction (emission direction) of the blood vessel based on a pulse wave transmitted from an ultrasound wave signal transmitter & receiver 221, concurrently, receives the reflected wave (ultrasound echo) thereof, and transmits the reflected wave to the ultrasound wave signal transmitter & receiver 221 as an ultrasound echo signal through a connector/adaptor unit 202 and a rotary joint 211.

The scanner & pull-back unit 102 includes a rotary drive apparatus 120 provided with a rotary joint 211 and a linear drive apparatus 130. The transmitting and receiving unit 201 inside the probe unit 101 is freely rotatably mounted by way of a rotary joint 211 coupling between a non-rotation unit and a rotation unit, and it is driven rotationally by a radial scanning motor 213. As the transmitting and receiving unit 201 is rotated inside the blood vessel centering around the axis of the probe unit 101, the ultrasound wave signal is scanned in the circumferential direction and based on this, it is possible to obtain ultrasound echo signals necessary for visualization of a cross-sectional image at a predetermined position inside the blood vessel.

The operation of the radial scanning motor 213 is controlled based on a control signal transmitted from a signal processing unit 225 through a motor control circuit 226, i.e., control means. Also, the rotary angle of the radial scanning motor 213 is detected by an encoder unit 214. An output pulse which is outputted in the encoder unit 214 is inputted to the signal processing unit 225 through motor control circuit 226 and is utilized for the construction of the cross-sectional image and the longitudinal-sectional image (details are described later).

The scanner & pull-back unit 102 further includes a linear drive apparatus 130 and defines axial direction motion of the transmitting and receiving unit 201 based on an input or instruction from a signal processing unit 225. The control circuit (driver) of the linear drive motor 131 is inside the linear drive apparatus 130. The radial scanning motor 213 and the linear drive motor 131 can either be connected detachably or constituted integrally.

The ultrasound wave signal transmitter & receiver 221 includes a transmitting circuit and a receiving circuit. The transmitting circuit transmit a pulse wave to the transmitting and receiving unit 201 inside the probe unit 101 based on a control signal transmitted from a signal processing unit 225.

Also, the receiving circuit receives an ultrasound echo signal detected by the transmitting and receiving unit 201 inside the probe unit 101. The received ultrasound echo signal is amplified by an amplifier 222.

Further, in the A/D converter 224, the ultrasound echo signal outputted from the amplifier 222 is subjected to sampling and digital data (ultrasound echo data) of one line is generated.

The ultrasound echo data of one line unit which are generated in the A/D converter 224 are inputted to a signal processing unit 225. In the signal processing unit 225, ultrasound echo data are detected, line data are generated and thereafter, cross-sectional images at respective positions inside the blood vessel are visualized based on the line data and then, are outputted to an LCD monitor 227 (corresponding to reference number 113 of FIG. 1A). The line data used for the visualization of the cross-sectional images (or visualized cross-sectional images themselves) are stored readably inside the signal processing unit 225 and in a case in which instruction is inputted by a user through the instruction input unit 228, it is assumed that the line data are to be redisplayed on the LCD monitor 227 as cross-sectional images. The line data is defined as data array which makes a line from center of the cross-sectional image to edge of the cross-sectional image.

Here, in the signal processing unit 225 relating to this embodiment disclosed by way of example, it is assumed that when storing line data (or cross-sectional images), they are stored by being correlated with the count value of the pulse signal outputted from the moving amount detector 132 of the linear drive apparatus 130. The details of these processes in the signal processing unit 225 are described later.

4. Operational and Functional Features of Optical Coherent Tomography Apparatus Next, within an imaging apparatus for diagnosis 100 relating to this embodiment described as one example of the apparatus, main functional or operational features of an optical coherent tomography apparatus for diagnosis will be explained referring to FIG. 3.

Reference numeral 309 indicates a low coherent light source of a super high luminance light-emitting diode or the like. The low coherent light source 309 outputs a low coherent light which presents coherence only in such a short distance range that the wavelength thereof is around 1310 nm and the coherent-able distance (coherent length) thereof is around several μm to ten and several μm.

Consequently, in a case in which this light is split into two lights (light paths) which are thereafter mixed or brought together, interference light is detected in a case in which difference of the two optical path lengths from the split point to the mixed point is within a short distance range of around several μm to ten and several μm, and in a case in which the difference of the optical path lengths is larger than that, interference light is not detected.

The light of the low coherent light source 309 enters one end of a first single mode fiber 327 and is transmitted to the distal end surface side. The first single mode fiber 327 is coupled with a second single mode fiber 328 and a third single mode fiber 331 optically by a photo coupler unit 308 on the way.

The photo coupler unit refers to an optical component which can split one optical signal into two or more outputs, which can couple two or more inputted optical signals into one output and the like, and it is possible for the light of the low coherent light source 309 to be transmitted by being split into maximum three optical paths depending on aforesaid photo coupler unit 308.

There is provided, on the distal end side from the photo coupler unit 308 of the first single mode fiber 327, the scanner & pull-back unit 102. There is provided, in the inside of the rotary drive apparatus 120 of the scanner & pull-back unit 102, an optical rotary joint 303 which couples between a non-rotation unit and a rotation unit and which transmits light.

Further, the distal end side of a fourth single mode fiber 329 inside the optical rotary joint 303 is freely detachably connected with a fifth single mode fiber 330 of the probe unit 101 through a connector/adaptor unit 302. Thus, the light from the low coherent light source 309 is transmitted to the fifth single mode fiber 330 which is connected to the inside of the imaging core 301 which repeats transmission and reception of the light and which is drivable rotationally.

The light transmitted to the fifth single mode fiber 330 is illuminated with respect to the biological tissue inside the blood vessel from the distal end side of the transmitting and receiving unit 301 while being scanned radially. Then, a portion of the reflected light scattered at the surface or in the inside of the biological tissue is taken-in or received by the transmitting and receiving unit 301 and returns to the first single mode fiber 327 side by way of the opposite optical path, and a portion thereof moves to the second single mode fiber 328 side by the photo coupler unit 308, and is emitted from one end of the second single mode fiber 328, whereby it is light-received by a photo detector (for example, photodiode 310).

The rotation unit side of the optical rotary joint 303 is driven rotationally by a radial scanning motor 305 arranged inside a rotary drive apparatus 120. Also, the rotary angle of the radial scanning motor 305 is detected by an encoder unit 306. Further, the scanner & pull-back unit 102 is provided with a linear drive apparatus 130 and defines axial direction motion of the transmitting and receiving unit 301 based on an instruction from a signal processing unit 314. Note that the control circuit (driver) of the linear drive motor 131 is placed inside the linear drive apparatus 130, but depiction thereof in the diagram here is omitted.

It is possible for the radial scanning motor 305 and the linear drive motor 131 to be connected detachably or to be constituted integrally.

On the other hand, the distal end side (reference light path) from the photo coupler unit 308 of the third single mode fiber 331 is provided with a variable mechanism of optical path length 316 for changing the optical path length of the reference light.

This variable mechanism of optical path length 316 is provided with a first optical path length changing means for changing, in a high-speed manner, the optical path length corresponding to a measurement range in the depth direction (emission direction of measurement light) of the biological tissue, and a second optical path length changing means for changing the optical path length corresponding to fluctuations in the length thereof so as to be able to absorb fluctuation of the length of individual probe unit 101 in case the probe unit 101 is exchanged for another probe unit.

There is arranged a mirror 319 which faces the distal end of the third single mode fiber 331 and which is mounted on an one-axis stage 320 together with this distal end, through a collimating lens 321 freely movable in the direction shown by an arrow 323. Also, there is mounted a minute angle rotatable galvanometer 317 as a first optical path length changing means through this mirror 319 and a corresponding lens 318. This galvanometer 317 is rotated in a high-speed manner in the arrow 322 direction depending on a galvanometer controller 324.

The galvanometer 317 is a meter which reflects the light depending on a mirror of the galvanometer and is constituted such that the mirror mounted on a movable portion thereof rotates high-speedily by applying an alternating-current drive signal to the galvanometer which functions as a reference mirror.

More specifically, a drive signal is applied with respect to the galvanometer 317 from the galvanometer controller 324 and by rotating in a high-speed manner in the arrow 322 direction caused by the drive signal, the optical path length of the reference light changes in a high-speed manner by as much as the optical path length corresponding to an measurement range in the depth direction of the biological tissue. One cycle of this change of the optical path difference becomes a period for obtaining the interference light for one line.

On the other hand, in case of exchanging the probe unit 101, the one-axis stage 320 functions as a second optical path length changing means having as much as a variable range of the optical path length, which can absorb the fluctuation of the optical path length of the probe unit 101. The one-axis stage 320 also functions as an adjusting means for adjusting an offset. For example, even in a case in which the distal end of the probe unit 101 is not closely-attached to the surface of the biological tissue, it is possible, by minutely changing the optical path length depending on the one-axis stage 320, to set a state of interfering with the reflected light from the surface position of the biological tissue.

The light whose optical path length is changed by the variable mechanism of optical path length 316 is mixed with the light obtained from the first single mode fiber 327 side by the photo coupler unit 308 provided on the way of the third single mode fiber 331 and is light-received by a photodiode 310 as an interference light.

The interference light light-received in the photodiode 310 in this manner is photoelectrically converted, is amplified by an amplifier 311 and thereafter, is inputted to a demodulator 312.

In the demodulator 312, a demodulation process for extracting only a signal component of the interference light is performed and an output thereof is inputted to an A/D converter 313.

In the A/D converter 313, the interference light signal is subjected to sampling, for example, by 200 points and digital data of one line ("interference light data") are generated. In this case, the sampling frequency becomes a value dividing one scan time period of the optical path length by 200.

The interference light data of one line unit which are generated in the A/D converter 313 are inputted to a signal processing unit 314. In the signal processing unit 314, cross-sectional image and longitudinal-sectional image (details thereof are described later) at respective positions inside the blood vessel are visualized based on the interference light data (line data) in the depth direction of the biological tissue and thereafter, they are outputted to an LCD monitor 315 (corresponding to reference numeral 113 in FIG. 1). The line data used for the visualization of the cross-sectional images (or visualized cross-sectional images themselves) are stored readably inside the signal processing unit 314 and it is assumed that they are to be redisplayed as cross-sectional images on the LCD monitor 315 in a case in which an instruction input is inputted from the user through the instruction input unit 334.

Here, in the signal processing unit 314 relating to this embodiment disclosed by way of example, it is assumed, on an occasion of storing the line data (or cross-sectional images), that they are to be store by being correlated with the count value of the pulse signal outputted from the moving amount detector 132 of the linear drive apparatus 130. Details of these processes in the signal processing unit 314 are discussed later.

Further, the signal processing unit 314 is connected with an optical path length adjusting means control apparatus 326 and controls the position of the one-axis stage 320 is carried out through the optical path length adjusting means control apparatus 326. Also, the signal processing unit 314 is connected with a motor control circuit 325 and controls the rotary drive of the radial scanning motor 305.

Also, the signal processing unit 314 is connected with a galvanometer controller 324 for controlling scan of the optical path length of the reference mirror (galvanometer mirror) and receives a drive signal from the galvanometer controller 324. In the motor control circuit 325, synchronization is taken with the galvanometer controller 324 by using the drive signal received by the signal processing unit 314.

5. Functional or Operational Features of Optical Frequency Domain Imaging Apparatus Utilizing Wavelength Sweep Next, within the imaging apparatus for diagnosis 100 relating to this embodiment disclosed by way of example, it will be explained with respect to a main functional constitution of the optical frequency domain imaging (OFDI) apparatus for diagnosis utilizing wavelength sweep by using FIG. 4.

Figure 4:
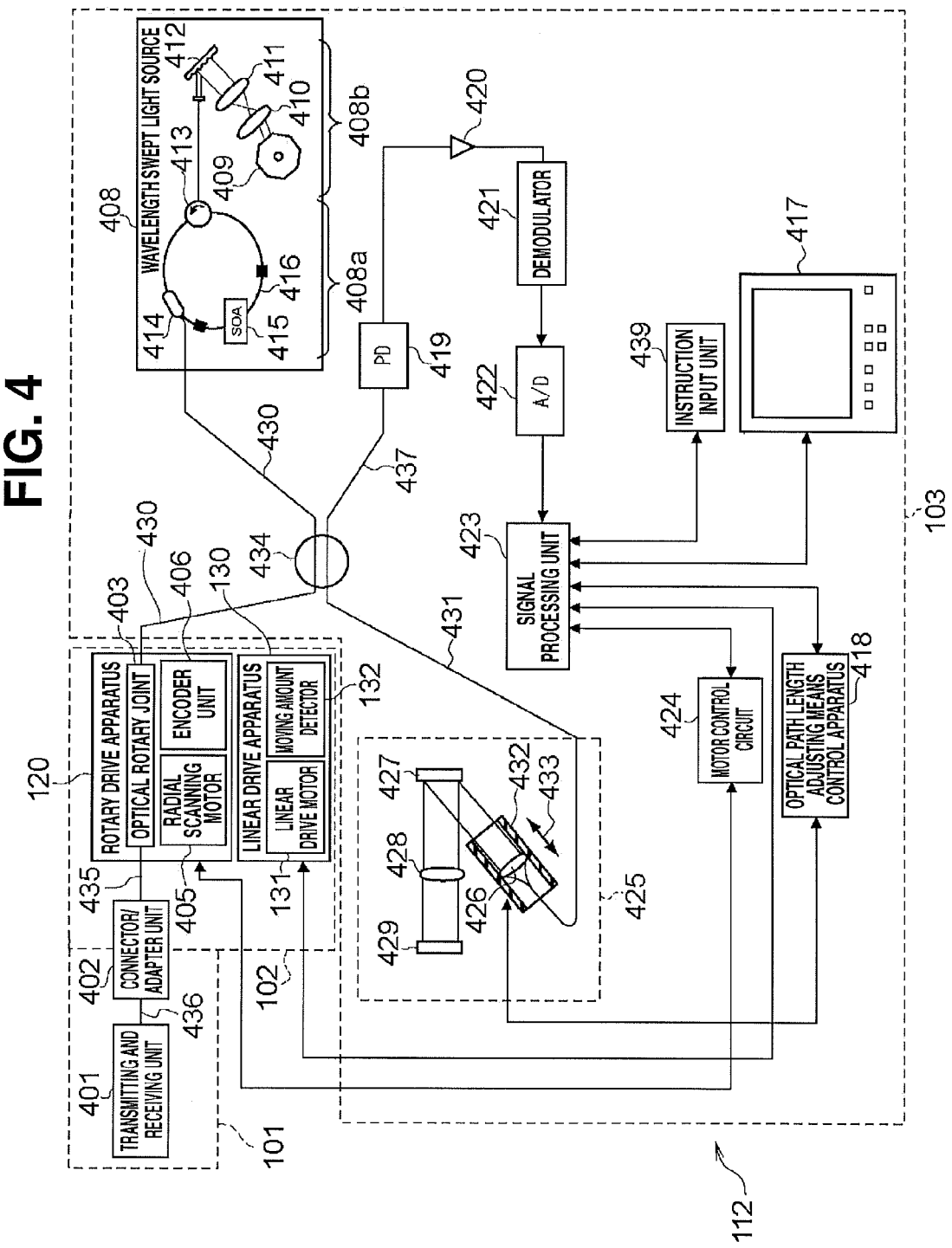
FIG. 4 is a diagram showing a functional constitution of an optical frequency domain imaging apparatus for diagnosis utilizing wavelength sweep.

FIG. 4 is a diagram showing a functional constitution of the optical frequency domain imaging apparatus utilizing wavelength sweep 100.

A reference numeral 408 indicates a wavelength swept light source and a swept laser is used thereto. The wavelength swept light source 408 using the wept Laser is one kind of an extended-cavity laser which is composed of an optical fiber 416 coupled with a SOA 415 (semiconductor optical amplifier) in a ring shape and a polygon scanning filter (408b).

The light outputted from the SOA 415 advances inside the optical fiber 416 and enters into the polygon scanning filter 408b and here, the wavelength selected light is amplified by the SOA 415 and finally, is outputted from a coupler 414.

In the polygon scanning filter 408b, the wavelength is selected by using the combination of a diffraction grating 412 for light-splitting the light and a polygon mirror 409. Specifically, the light light-split by the diffraction grating 412 is focused on the surface of the polygon mirror 409 by two pieces of lens (410, 411). Thus, only the light having wavelength, which is perpendicular to the polygon mirror 409 returns to the same optical path and is outputted from the polygon scanning filter 408b, so that by rotating the mirror, it is possible to carry out time sweep of the wavelength.

With respect to the polygon mirror 409, for example, a 32-facets mirror is used and a rotation speed thereof is around 50000 rpm. Depending on a wavelength sweep system in which the polygon mirror 409 and the diffraction grating 412 are combined, it becomes possible to employ wavelength sweep of a high speed and a high power output.

The light of the wavelength swept light source 408 which is outputted from the coupler 414 enters one end of a first single mode fiber 430 and transmitted to the distal end side. The first single mode fiber 430 is coupled optically with a second single mode fiber 437 and a third single mode fiber 431 in a photo coupler unit 434 on the way. Therefore, it is possible for the light of the wavelength swept light source 408 to be transmitted by being split into maximum three optical paths depending on this photo coupler unit 434.

There is provided, on the distal end side from the photo coupler unit 434 of the first single mode fiber 430, with an optical rotary joint 403, which couples between a non-rotation unit and a rotation unit and which transmits the light, inside the rotary drive apparatus 120.

Further, the distal end side of a fourth single mode fiber 435 inside the optical rotary joint 403 is connected with a fifth single mode fiber 436 of the probe unit 101 freely detachably through a connector/adapter unit 402. Thus, the light from the wavelength swept light source 408 is transmitted to the fifth single mode fiber 436 connected inside the transmitting and receiving unit 401 which repeats transmission and reception of the light and which is drivable rotationally.

The transmitted light is emanated while being radially scanned from the distal end side of the transmitting and receiving unit 401 with respect to the biological tissue of inside the body lumen. Then, a portion of the reflected light scattered at the surface or in the inside of the biological tissue is taken-in by the transmitting and receiving unit 401 and returns to the first single mode fiber 430 side by way of the opposite optical path. Further, a portion thereof is moved to the second single mode fiber 437 side by the photo coupler unit 434, is emanated from one end of the second single mode fiber 437, and is light-received by a photo detector (for example, photodiode 419).

The scanner & pull-back unit 102 includes a rotary drive apparatus 120 arranged with an optical rotary joint 403. The transmitting and receiving unit 401 inside the probe unit 101 is mounted freely rotatably by the optical rotary joint 403 coupling between a non-rotation unit and a rotation unit, and it is driven rotationally by a radial scanning motor 405. By a fact that the transmitting and receiving unit 401 is rotated inside the blood vessel centering around the axis of the probe unit 101, the measurement light is scanned in the circumferential direction and depending on this, it is possible to obtain interference light signals necessary for visualization of cross-sectional image at a predetermined position inside the blood vessel.

Note that the operation of the radial scanning motor 405 is controlled based on a control signal transmitted from a signal processing unit 423 through a motor control circuit 424. Also, rotary angle of the radial scanning motor 405 is detected by an encoder unit 406. An output pulse which is outputted in the encoder unit 406 is inputted to the signal processing unit 423 through the motor control circuit 424 and is utilized for the construction of the cross-sectional image and the longitudinal-sectional image (details will be described later). The scanner & pull-back unit 102 further includes a linear drive apparatus 130 and defines the axial direction movement of the transmitting and receiving unit 401 based on an instruction from a signal processing unit 423. Note that a control circuit (driver) of the linear drive motor 131 is assumed to be installed inside the linear drive apparatus 130 and the graphic indication thereof will be omitted here.

Note that it is possible for the radial scanning motor 405 and the linear drive motor 131 to be connected detachably or to be constituted integrally.

On the other hand, there is provided, on the distal end side from the photo coupler unit 434 of the third single mode fiber 431, with a variable mechanism of optical path length 425 for fine-adjusting the optical path length of the reference light.

This variable mechanism of optical path length 425 is provided with an optical path length changing means for changing the optical path length corresponding to the length of fluctuation thereof so as to be able to absorb fluctuation of the length of the individual probe unit in case of using the probe unit 101 by being exchanged.

The third single mode fiber 431 and a collimating lens 426 are provided on a freely movable one-axis stage 432 as shown by an arrow 433 in the optical axis direction thereof, and they form the optical path length changing means.

Specifically, the one-axis stage 432 functions as the optical path length changing means having as much as variable range of the optical path length so as to absorb fluctuation of the optical path length of the probe unit 101 in case of exchanging the probe unit 101. Further, the one-axis stage 432 functions also as an adjusting means for adjusting an offset. For example, also in a case in which the distal end of the probe unit 101 is not closely-attached to the surface of the biological tissue, it is possible, by minute-changing the optical path length depending on the one-axis stage 432, to set a state of interfering with the reflected light from the surface position of the biological tissue.

The light whose optical path length is fine-adjusted by the variable mechanism of optical path length 425 is mixed with the light obtained from the first single mode fiber 430 side by the photo coupler unit 434 provided on the way of the third single mode fiber 431 and is light-received by a photodiode 419 as an interference light.

The interference light light-received in the photodiode 419 in this manner is photoelectrically converted, is amplified by an amplifier 420 and thereafter, is inputted to a demodulator 421. In this demodulator 421, a demodulation process for extracting only a signal component of the interference light is performed and an output thereof is inputted to an A/D converter 422 as an interference light signal.

In the A/D converter 422, the interference light signal is subjected to sampling, for example, by 2048 points at 90 MHz and digital data (interference light data) of one line are generated. The reason the sampling frequency is set to be 90 MHz is based on an assumption that about 90% of the period of wavelength sweep (25.0 μsec) is to be extracted as digital data of 2048 points in case of setting the repetition frequency of wavelength sweep to be 40 kHz. The invention here is not limited by this aspect in particular.

The interference light data of one line unit, which are generated in the A/D converter 422 are inputted to the signal processing unit 423. In the signal processing unit 423, the interference light data are frequency-decomposed by FFT (Fast Fourier Transform) and data (line data) in the depth direction are generated, and by coordinate-converting these data, cross-sectional images at respective positions inside the blood vessel are visualized and thereafter, outputted to an LCD monitor 417 (corresponding to reference numeral 113 in FIG. 1). Also, concurrently, longitudinal-sectional images (details thereof will be described later) are visualized by using the generated line data and outputted to the LCD monitor 417. The line data used for the visualization of the cross-sectional image (or the visualized cross-sectional image itself) is stored readably inside the signal processing unit 423 and it is assumed that they are to be redisplayed on the LCD monitor 417 as the cross-sectional image in a case in which an instruction is inputted from a user through the instruction input unit 439.

Here, in the signal processing unit 423 relating to this embodiment disclosed as an example, on an occasion of storing the line data (or cross-sectional image), it is assumed that they are to be stored by being correlated with the count value of the pulse signal outputted from the moving amount detector 132 of the linear drive apparatus 130. Note that details of these processes in the signal processing unit 423 are discussed later.

Further, the signal processing unit 423 is connected with the optical path length adjusting means control apparatus 418. The signal processing unit 423 controls the position of the one-axis stage 432 mentioned above through the optical path length adjusting means control apparatus 418.

6. Radial Operation of Transmitting and Receiving Unit

Figure 5A:
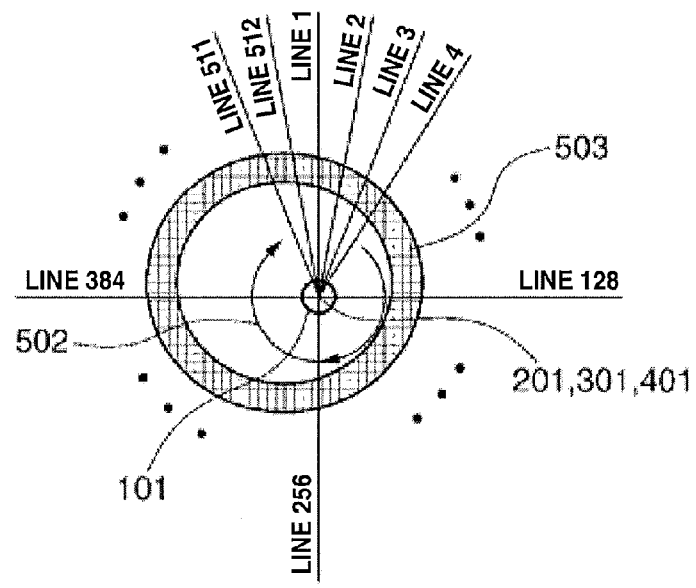
FIG. 5A is a schematic diagram for explaining a radial operation of a transmitting and receiving unit.
Figure 5B:
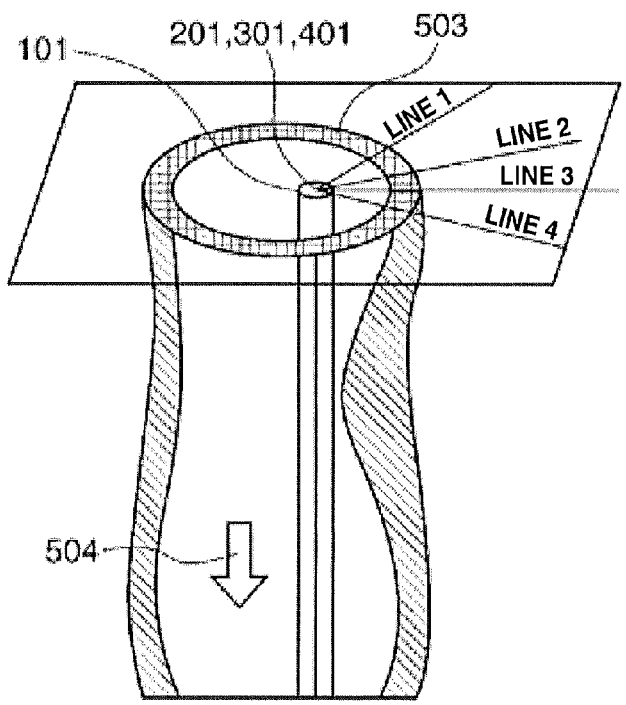
FIG. 5B is a schematic diagram for explaining a radial operation of a transmitting and receiving unit.

FIG. 5A and FIG. 5B are schematic diagrams explaining a radial operation of the transmitting and receiving unit and are a perspective and cross-sectional views of the blood vessel respectively in a state in which the probe unit 101 is inserted.

In FIG. 5A, a reference numeral 503 shows a blood vessel cross-section in which the probe unit 101 is inserted. As described above, to the distal end inside of the probe unit 101, the transmitting and receiving unit (201, 301, 401) are attached, which rotate in an arrow 502 direction by the radial scanning motor 213, 305, 405.

In the transmitting and receiving unit (201, 301, 401), transmission/reception of ultrasound or measurement light is carried out at each rotary angle. Lines 1, 2, . . . 512 show the transmission direction of the ultrasound or the measurement light at each rotary angle. In the imaging apparatus for diagnosis 100 relating to this embodiment disclosed by way of example, while the transmitting and receiving unit (201, 301, 401) rotates by 360 degrees at a predetermined blood vessel cross-section 503, transmission/reception of the ultrasound or the measurement light is carried out 512 times intermittently. Note that the number of times the transmission/reception of the ultrasound or the measurement light carried out during the rotation by 360 degrees is not limited by this aspect in particular and it is assumed that the number of times thereof is settable arbitrarily.

Such transmission/reception of the ultrasound or the measurement light is carried out while proceeding inside the blood vessel toward the arrow 504 direction (FIG. 5B). A scan (scanning) for repeating the transmission/reception of the signal by the transmitting and receiving unit (201, 301, 401) in each blood vessel cross-section according to the proceeding of the transmitting and receiving unit (201, 301, 401) toward the arrow 504 direction is generally referred to as "radial scan (radial scanning)".

7. Detailed Construction of Signal Processing Unit

Figure 6:
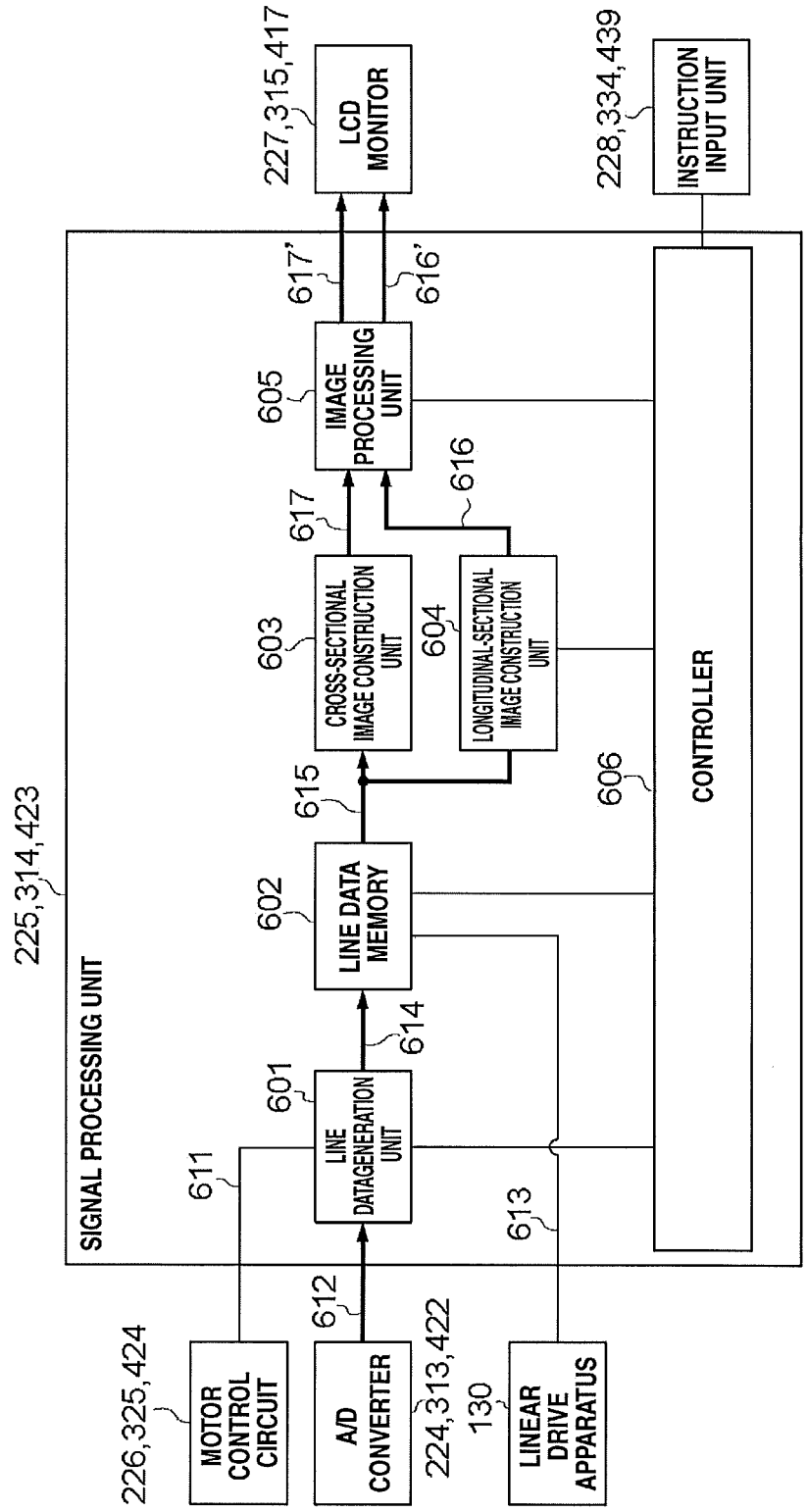
FIG. 6 is a diagram showing a detailed constitution of a signal processing unit and a related function block.
Figure 7:
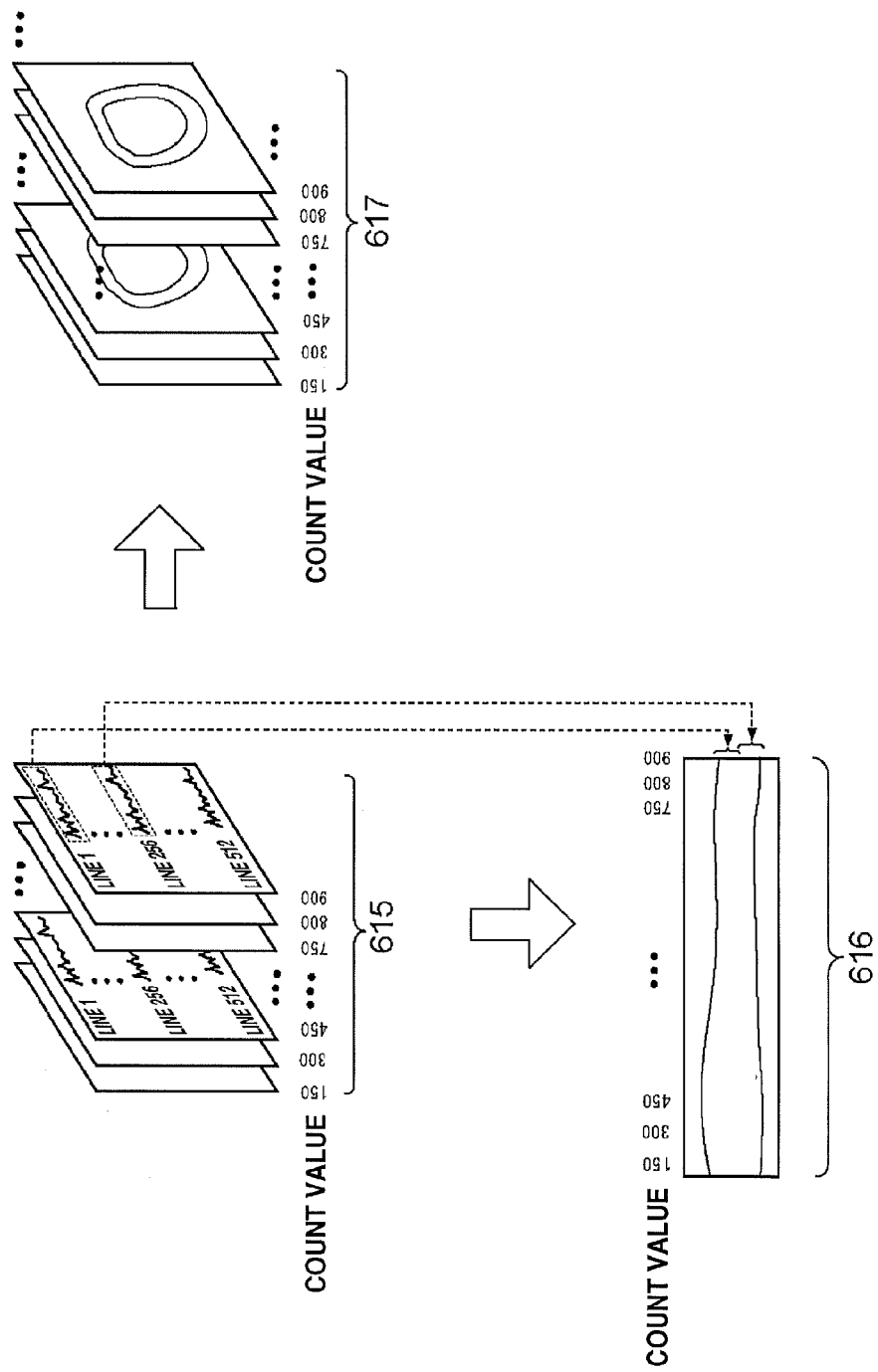
FIG. 7 is a diagram showing an outline of a process in a signal processing unit.
Figures 8, 9:
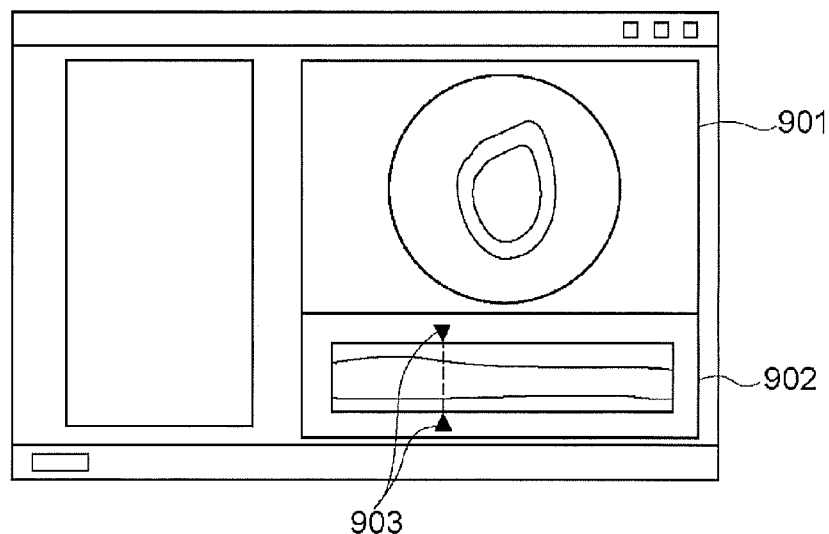
FIG. 8 is a diagram showing one example of line data stored in a line data memory.
FIG. 9 is a diagram showing a display example of an LCD monitor.

The description which follows explains, in the signal processing unit 225, 314, 423 of the imaging apparatus for diagnosis 100, a process or operation involving constructing a cross-sectional image and a longitudinal-sectional image, and a functional/operational constitution for realizing a storage process storing line data in the signal processing unit 225, 314, 423 by using FIG. 6, FIG. 7 and FIG. 8. It is possible for the construction process and the storage process explained hereinafter to be realized using a hardware for exclusive use and it is also possible for the function/operation of each portion to be realized by software (by executing a machine readable non-transitory computer program stored in a computer-readable medium). The signal processing unit 225, 314, 423 performs as storage means, construction means, readout means, calculation means and reconstruction means.

FIG. 6 is a diagram showing features and aspect of the apparatus for realizing a construction process and a storage process in the signal processing unit 225, 314, 423 of the imaging apparatus for diagnosis 100 and showing functional blocks related thereto. Also, FIG. 7 schematically shows a specific example of the construction process and the storage process carried out by the signal processing unit 225, 314, 423. Further, FIG. 8 is a diagram showing an aspect of storing line data generated in the signal processing unit 225, 314, 425 into a line data memory.

Figure 3:
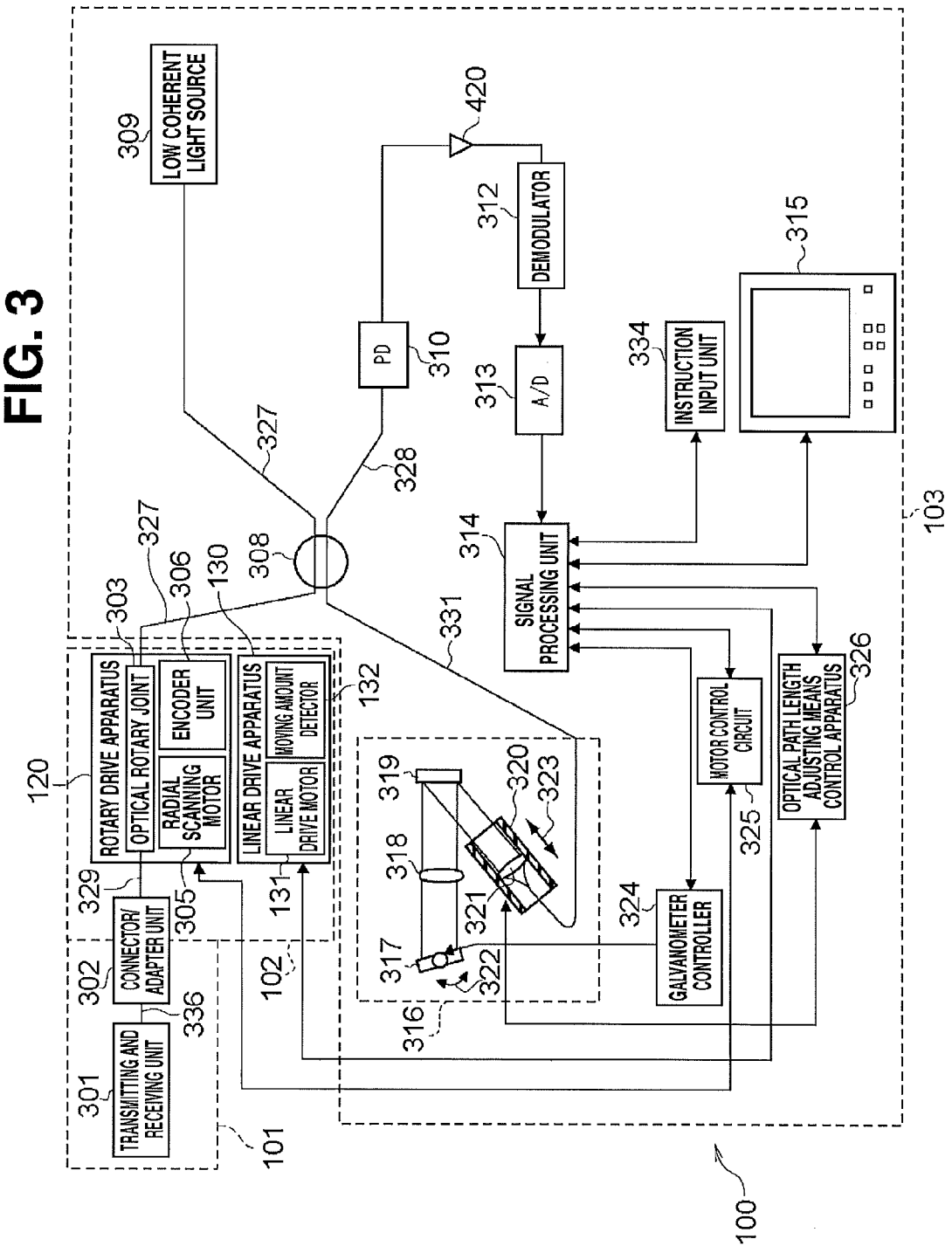
FIG. 3 is a diagram showing a functional constitution of an optical coherent tomography apparatus for diagnosis.

To simplify the explanation, the following discussion considers an embodiment in which the signal processing unit in the imaging apparatus for diagnosis is a signal processing unit 314 of a optical coherent tomography apparatus 100 (FIG. 3). In the case of other imaging apparatus for diagnosis, the configuration is similar, so that the explanation thereof is not repeated.

The interference light data generated in the A/D converter 313 is processed in a line data generation unit 601 shown in FIG. 6 such that the number of lines per one rotation of the radial scanning motor becomes 512 lines by using the signal of the encoder unit 306 of the radial scanning motor 305, which is outputted from the motor control circuit 325.

The example described here is discussed in terms of the cross-sectional image being constructed out of 512 lines, but the number of lines is not limited in this regard.

The line data 614 outputted from the line data generation unit 601 is stored in the line data memory 602 for every one rotation of the radial scanning motor based on an instruction from the control unit 606. At that time, in the controller 606 (which is an example of a receiving means configured to receive information relating to the axial direction moving amount of the transmitting and receiving unit from a predetermined reference position), a pulse signal outputted from a moving amount detector 132 of the linear drive apparatus 130 is counted beforehand and thereafter, when storing the line data 614 into the line data memory 602, the storing is carried out by being correlated with count values when generating the respective line data 614 (numeral 615 in FIG. 7 shows an aspect in which line data 614 are stored by being correlated with the count value for every one rotation (512 lines) of the radial scanning motor, and FIG. 8 shows a specific correlation). The memory 602 is an example of storage means configured to store the respective constructed cross-sectional images through correlation with information relating to moving amounts in the axial direction from the predetermined reference position of the transmitting and receiving unit.

A case was explained here in which the line data memory 602 is arranged and the line data 614 is stored by correlating it with the count value of the pulse signal outputted from the moving amount detector 132 of the linear drive apparatus 130, but the present invention is not limited in this regard. For example, a constitution is possible in which a cross-sectional image data memory is arranged behind the cross-sectional image construction unit 603 and the cross-sectional image 617 is stored in such a manner as to be correlated with the count value of the pulse signal outputted from the moving amount detector 132 of the linear drive apparatus 130.

Returning to the explanation of FIGS. 6-8, based on the instruction from the control unit 606, the line data 615 stored by being correlated with the count value is subjected to various kinds of processes (line addition-averaging process, filtering process and the like) in the cross-sectional image construction unit 603 and thereafter, is sequentially outputted as cross-sectional image 617 by being Rθ-converted. A reference numeral 617 of FIG. 7 shows one example of multiple cross-sectional images correlated with the count value.

Further, in the image processing unit 605, image processing for displaying on the LCD monitor 315 is applied and thereafter, it is outputted to the LCD monitor 315 as a cross-sectional image 617'.

Also, the line data 615 stored by being correlated with the count value is read out by the longitudinal-sectional image construction unit 604 based on the instruction from the control unit 606. In the longitudinal-sectional image construction unit 604, a longitudinal-sectional image 616 is constructed using the read out line data 615. The longitudinal-sectional image construction unit 604 is an example of construction means for constructing a longitudinal-sectional image based on data of the multiple cross-sectional image stored in the storage means.

Here as an example, an example was explained in which a longitudinal-sectional image is constructed from the line data 615, but the present invention is not limited in this regard as it is possible to employ an arrangement in which a longitudinal-sectional image is constructed from the cross-sectional image 617.

Reference numeral 616 in FIG. 7 shows an aspect in which a longitudinal-sectional image is constructed based on the line data 615 in the longitudinal-sectional image construction unit 604. As shown in this figure, in the longitudinal-sectional image construction unit 604, first, with respect to the respective line data 615 (line data from line 1 to line 512 are included respectively) in the read out respective count values, the predetermined line data (line data by two lines, which correspond to arbitrary coordinate axis passing through center coordinate of cross-sectional image in case of constructing cross-sectional image, (line data having relation of 180° each other)) are extracted respectively (in the example of FIG. 7, line data at line 1 and line 256 are extracted). Subsequently, the line data at every two lines which are extracted from the respective line data 615 are aligned at the position in the axial direction, which corresponds to the count value correlated with the respective line data 615. Thus, the longitudinal-sectional image 616 in which the horizontal axis denotes the count value and the vertical axis denotes the line data (specifically, pixel value of line data) is constructed.

In this manner, by employing a constitution in which the image value of the extracted line data is aligned at the position in the axial direction, which corresponds to the count value correlated with the respective line data 615, it becomes possible to construct a longitudinal-sectional image corresponding to each position in the axial direction of the transmitting and receiving unit 301 with the start position of the radial operation being a reference position.

The constructed longitudinal-sectional image 616 is read out by the image processing unit 605 based on the instruction from the control unit 606, is subjected to image processing so as to be displayed on the LCD monitor 315, and then is outputted to the LCD monitor 315 as a longitudinal-sectional image 616'.

In the LCD monitor 315, the cross-sectional image 617' processed in the image processing unit 605 and the longitudinal-sectional image 616' are displayed in parallel. Also, the cross-sectional image 617' constructed using respective line data inside the line data memory 602, correlated with the same count value as that of the line data disposed at the position corresponding to the instruction inputted from the user through the instruction input unit 334, is redisplayed.

Set forth hereinafter is an explanation of aspects and details involving the display of the cross-sectional image 617' and the longitudinal-sectional image 616' on the LCD monitor 315, and the redisplay of the cross-sectional image 617' corresponding to the instruction inputted by the user through the instruction input unit 334.

8. Display Example in LCD Monitor and Instruction Input Unit

FIG. 9 is a diagram explaining display of the cross-sectional image 617' and the longitudinal-sectional image 616' in the LCD monitor 315 and redisplay of the cross-sectional image 617' corresponding to the instruction inputted by the user through the instruction input unit 334.

As shown in FIG. 9, the LCD monitor 315 includes a cross-sectional image display area 901 for displaying the cross-sectional image 617' and a longitudinal-sectional image display area 902 for displaying the longitudinal-sectional image 616'. In the cross-sectional image display area 901, a plurality of the cross-sectional images 617' generated along with the radial operation of the transmitting and receiving unit 301 are displayed sequentially in real time.

On the other hand, in the longitudinal-sectional image display area 902, the longitudinal-sectional image 616' is to be constructed gradually along with the radial operation of the transmitting and receiving unit 301 and the construction of the longitudinal-sectional image 616' continues until the radial operation stops.

In the longitudinal-sectional image display area 902, an indicator 903 for appointing a predetermined position in the axial direction is displayed and it is possible for the user to appoint or select the predetermined position in the axial direction of the longitudinal-sectional image 616' by moving the indicator 903 in the axial direction through the instruction input unit 334.

In the imaging apparatus for diagnosis 100 relating to this embodiment disclosed by way of example, the cross-sectional image 617' reconstructed by using the line data disposed at the position corresponding to the appointed position in the axial direction is constituted so as to be displayed inside the cross-sectional image display area 901. This makes it possible for the user to visually confirm the cross-sectional image 617' corresponding to the longitudinal or axial position by only appointing or selecting the position in the axial direction of the blood vessel. The controller 660 is an example of a reconstruction means for reconstructing the cross-sectional image as described.

In other words, in the conventional imaging apparatus for diagnosis, a redisplayed cross-sectional image does not make it possible for the user to accurately grasp the cross-sectional image as to which position the transmitting and receiving unit actually moved to in the axial direction of the blood vessel after the radial operation was started, whereas it becomes possible for the user here to visually confirm a cross-sectional image by correlation with a position in the axial direction of the blood vessel in the imaging apparatus for diagnosis relating to this embodiment disclosed by way of example.

9. Explanation of Operation Flow when Obtaining Cross-Sectional Image

Figure 10:
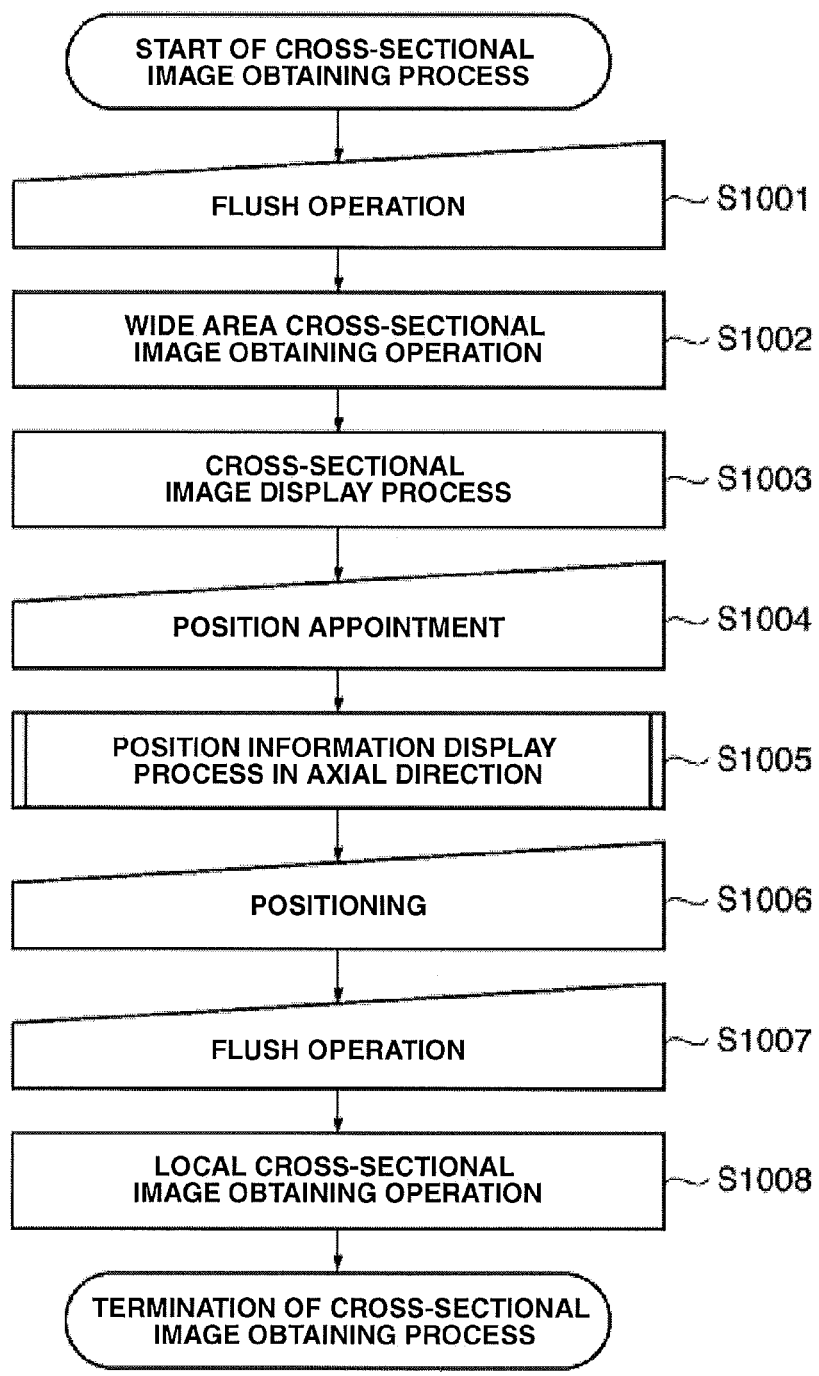
FIG. 10 is a diagram showing one example of an operation flow on an occasion when a cross-sectional image is obtained.

Set forth next, referring to FIG. 10, is a description of the operation or process flow when obtaining the cross-sectional image. The operation flow explained hereinafter is with respect to an example in which cross-sectional images inside a blood vessel are obtained using the optical coherent tomography apparatus or the optical frequency domain imaging apparatus for diagnosis utilizing wavelength sweep 100.

In step S1001, the user carries out a flush operation. The flush operation is an operation for removing blood inside a blood vessel beforehand in a region of the imaging target. Specifically, this refers to an operation in which a physiological saline, a lactated Ringer's solution, a contrast agent and the like are discharged from a guiding catheter (not shown) in which the transmitting and receiving unit 301 is stored and the blood inside the blood vessel at the imaging region is removed.

This is because the coherent light used in the optical coherent tomography apparatus or the optical frequency domain imaging apparatus for diagnosis utilizing wavelength sweep, whose wavelength is around 800 nm to 1550 nm, does not pass through the blood and so it is necessary to remove the blood inside the blood vessel beforehand in the imaging region on an occasion of visualization of a cross-sectional image of the blood vessel. Consequently, when visualizing a cross-sectional image by the optical coherent tomography apparatus or the optical frequency domain imaging apparatus for diagnosis utilizing wavelength sweep 100, a physiological saline, a lactated Ringer's solution, a contrast agent or the like are discharged from the probe unit 101 beforehand to carry out the flushing operation for removing the blood inside the blood vessel in the imaging region is carried out.

In step S1002, the user carries out an operation for obtaining a cross-sectional image in a wide range. Specifically, by carrying out a pullback in which the transmitting and receiving unit 301 is pulled out at an appropriate speed, a cross-sectional image is obtained over a wide range including the disorder portion (target area).

In step S1003, there is carried out a display process for displaying the cross-sectional image obtained with the wide range cross-sectional image obtaining operation to the LCD monitor 113. The display process is executed concurrently with the user performing the pullback of the transmitting and receiving unit 301 in the wide area cross-sectional image obtaining operation.

In step S1004, from the longitudinal-sectional image displayed along with the display of the cross-sectional image, the user appoints or selects a position which the user wants to display again by using the indicator 903 (appoint or identify the position which is supposed to be a disorder portion or portion of interest). In step S1005, a "positional information display process in axial direction" for redisplaying with respect to the cross-sectional image reconstructed by using the line data correlated with the same count value as that of the line data disposed at the position corresponding to the position appointed or identified in step S1004 is carried out.

Details of the "positional information display process in axial direction" in step S1005 will be described later. The controller 606 is an example of a readout means for identifying a user-identified position on the displayed longitudinal-sectional image and concurrently read outing from the storage means the cross-sectional image disposed at the identified position.

In step S1006, the transmitting and receiving unit 301 is moved to the position at which the redisplayed cross-sectional image was obtained in step S1005.

In step S1007, the user carries out the flush operation again. Then, after the flush operation, in step S1008, the user carries out an operation for obtaining a local cross-sectional image. Specifically, by pulling back the transmitting and receiving unit 301 with the position moved in step S1006 being set as the radial operation start position, a detailed cross-sectional image is obtained again with respect to the disorder portion.

By virtue of the process or operation flow described above, it is possible for the user to carry out an operation in which after a disorder portion (portion of interest) is confirmed based on a cross-sectional image obtained based on a wide area cross-sectional image obtaining operation, the transmitting and receiving unit is moved to the disorder portion and again a regional cross-sectional image obtaining operation is carried out with respect to the disorder portion, and thus it becomes possible to obtain a more detailed cross-sectional image with respect to the disorder portion.

10. Details of Positional Information Display Process in Axial Direction

Figure 11:
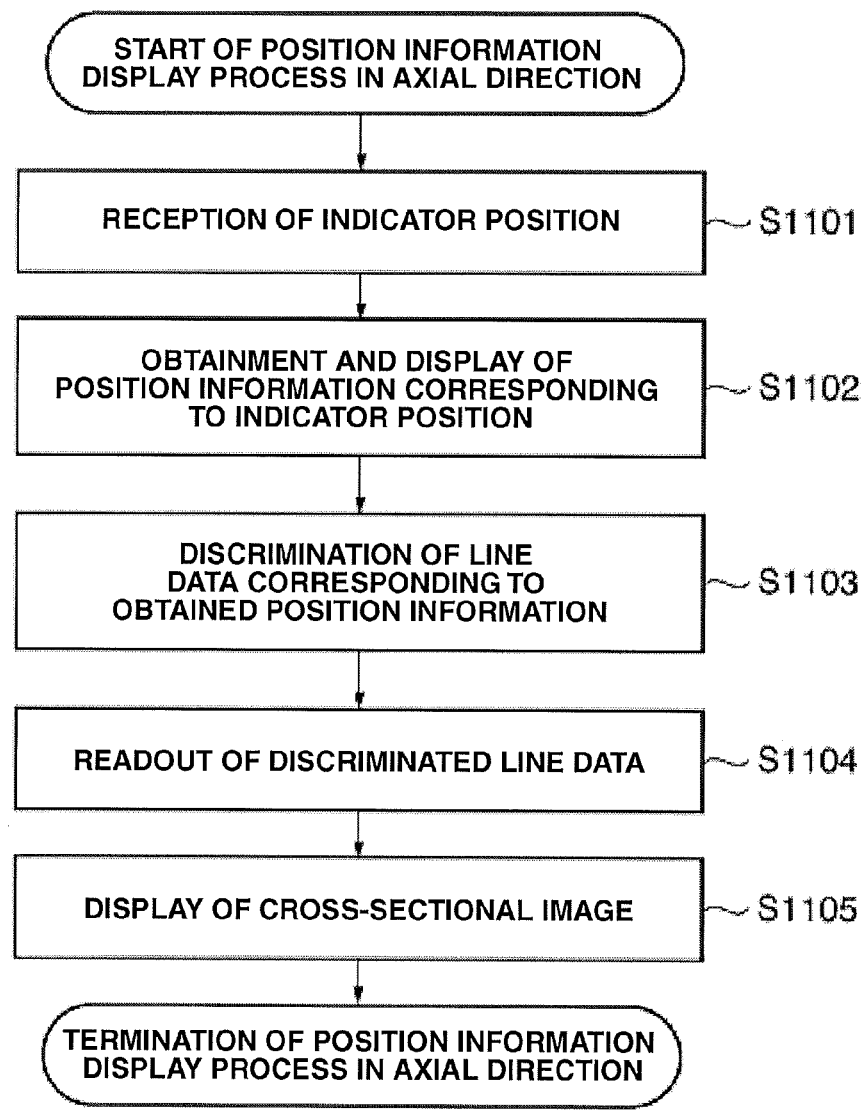
FIG. 11 is a flowchart showing a flow of a positional information display process in an axial direction.

The description will now explain the details of the positional information display process (step S1005 in FIG. 10) in an axial direction. FIG. 11 is a flowchart or process routine showing a detailed flow of a positional information display process in an axial direction.

In step S1101, the position of the indicator 903, which is appointed by the user on the longitudinal-sectional image, is identified.

In step S1102, by obtaining the count value of the line data disposed at the position corresponding to the position of the indicator 903 on the longitudinal-sectional image, which is identified in step S1101, positional information corresponding to the position of the indicator 903 is obtained and displayed. In a case in which the indicator is selected twice, positional information corresponding to two positions is obtained and displayed.

In step S1103, the line data corresponding to the positional information obtained in step S1102 are discriminated from among the line data stored in the line data memory 602 (see FIG. 8). Note that it is assumed that the line data corresponding to the positional information means the line data disposed at the position indicated by the positional information or the line data disposed at the nearest position to the position indicated by the positional information.

In step S1104, the line data correlated with the same count value as that of the line data discriminated in step S1103 is read out and in step S1105, the cross-sectional image reconstructed based on the read out line data is redisplayed on the LCD monitor 315. The controller 606 can be an example of a readout means for identifying a user-identified position on the displayed longitudinal-sectional image and concurrently reading out from the storage means the cross-sectional image disposed at the identified position.

As clear from the explanation mentioned above, the imaging apparatus for diagnosis according to this embodiment disclosed by way of example is constructed to correlate obtained line data with a count value of a pulse signal outputted from the linear drive apparatus of the scanner & pull-back unit and stored. Also, a longitudinal-sectional image is constructed using the line data and the count value, and is displayed.

Thus, in the imaging apparatus for diagnosis 100 relating to this embodiment, it becomes possible to redisplay, within the cross-sectional image display area, the cross-sectional image corresponding to the appointed or selected position in the axial direction on the longitudinal-sectional image.

In the conventional imaging apparatus for diagnosis, a redisplayed cross-sectional image does not make it possible for the user to accurately grasp, with respect to the cross-sectional image, the position to which the transmitting and receiving unit actually moved to in the axial direction of the blood vessel after the radial operation was started, whereas here it is possible for the user to visually confirm a cross-sectional image by correlation with a position in the axial direction of the blood vessel according to the imaging apparatus for diagnosis.

In this embodiment disclosed as an example, the reference position at the time when detecting the moving distance is made to be the start position of the radial operation, but it is not limited in this regard. For example, it is possible to make an arbitrary position such as the maximum forward position, the maximum backward position or the like of the linear drive apparatus in the scanner & pull-back unit be the reference position of the linear drive apparatus.

Second Embodiment

The first embodiment of the apparatus and method discussed above is configured to display one indicator 903, but the present invention is not limited by this. For example, it is possible to employ a construction in which two indicators 903, or two or more indicators 903 are displayed. Also, in a case in which two indicators 903 are displayed, it is also possible to employ an arrangement in which two cross-sectional images corresponding to the positions of two points appointed by the indicator 903 respectively are displayed and concurrently, the distance between the two points is calculated and displayed.

By employing such a constitution, for example, on an occasion when the stent lying in the lesion is selected, the positions of arbitrary two points are appointed and while seeing two cross-sectional images corresponding to the positions of the appointed two points respectively, it is possible to carry out such an operation in which the most suitable stent is selected.

Third Embodiment

Step S1006 of the first embodiment mentioned above employs an arrangement in which the transmitting and receiving unit 301 is moved to the position at which the cross-sectional image redisplayed in step S1005 was obtained, based on the user's operation, but the present invention is not limited in this regard. For example, it is possible to employ an arrangement in which the transmitting and receiving unit moves automatically by controlling the axial direction motion. The description below will explain this alternative in terms of an embodiment disclosed by way of example.

1. Display Example and Instruction Input Unit in LCD Monitor

Figure 12:
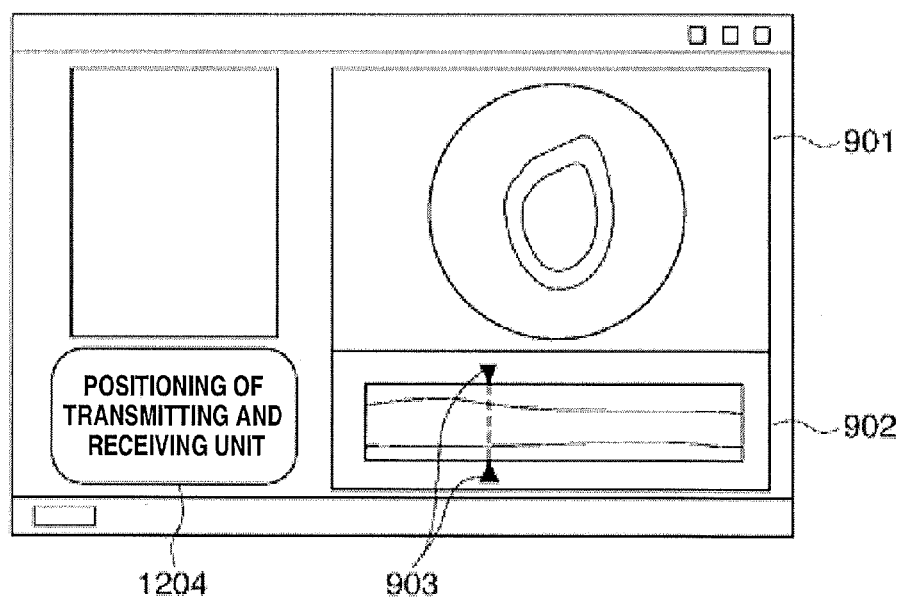
FIG. 12 is a diagram showing a display example of an LCD monitor.

FIG. 12 is a diagram explaining display of the cross-sectional image 617' and the longitudinal-sectional image 616' in the LCD monitor 315, redisplay of the cross-sectional image 617' corresponding to an instruction inputted from the user through the instruction input unit 334, and movement of the transmitting and receiving unit 301 to the position at which the redisplayed cross-sectional image 617' was imaged. Note that, here, an explanation is to be given centering around the differences from FIG. 9.

As shown in FIG. 12, the LCD monitor 315 includes a transmitting and receiving unit positioning button 1204. When the transmitting and receiving unit positioning button 1204 is operated (e.g., pushed down), the axial direction motion of the transmitting and receiving unit 301 is controlled such that the transmitting and receiving unit 301 moves to the position of the transmitting and receiving unit 301 at the time when the cross-sectional image 617' displayed on the cross-sectional image display area 901 at present was imaged.

2. Details of Positioning Process of Transmitting and Receiving Unit

Figure 13:
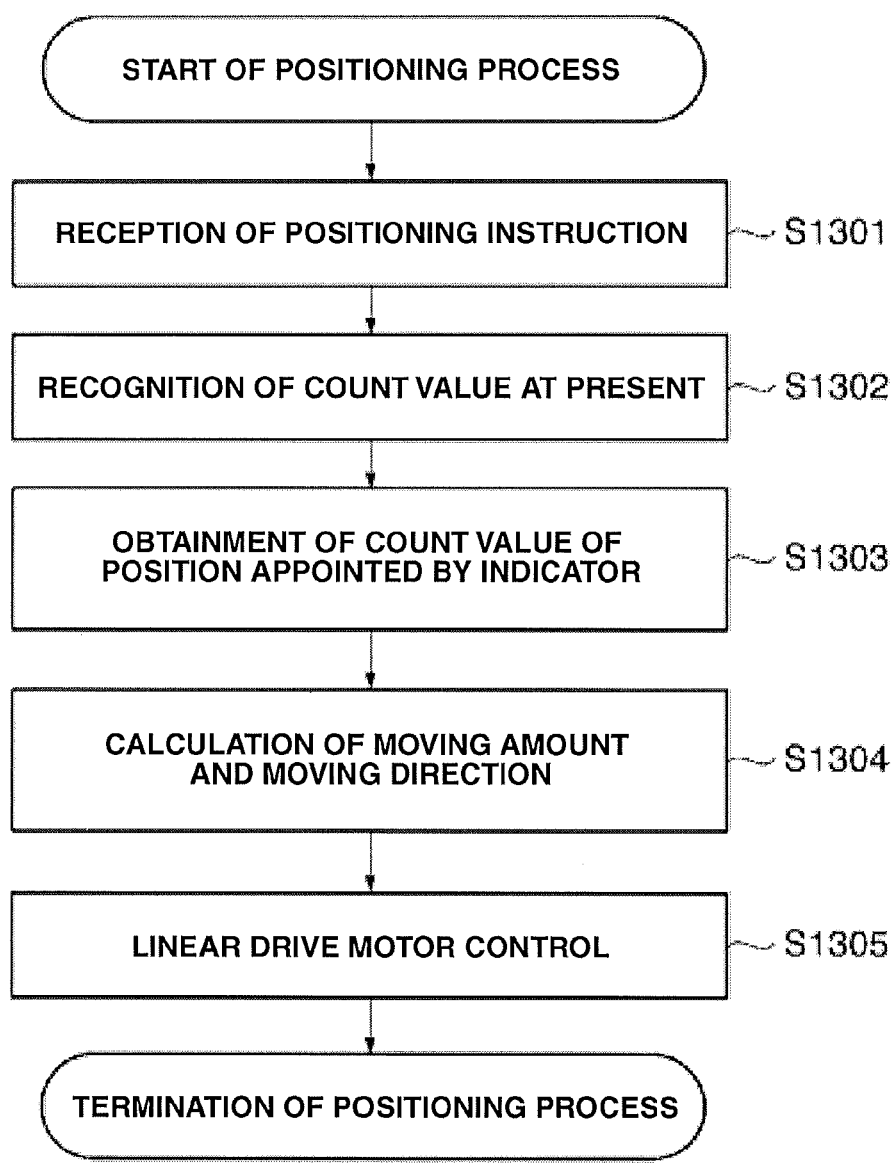
FIG. 13 is a flowchart showing a flow of a positioning operation.

Set forth next is a description of a positioning process (positioning process according to this embodiment carried out in step S1006 of FIG. 10) of the transmitting and receiving unit in this embodiment. FIG. 13 is a flowchart showing a detailed flow of a positioning process of this embodiment.

In step S1301, in the LCD monitor 315, in a case in which the transmitting and receiving unit positioning button 1204 is operated or pushed down by the user, this is accepted.

In step S1302, the count value corresponding to the position (present position) of the transmitting and receiving unit at the time point when the transmitting and receiving unit positioning button 1204 is operated or pushed down is recognized.

In step S1303, when the transmitting and receiving unit positioning button 1204 is operated or pushed down, the count value correlated with the line data which are disposed at the position appointed or indicated by the indicator 903 is obtained.

In step S1304, the count value recognized in step S1302 and the count value obtained in step S1303 are compared and the moving amount and the moving direction for moving the transmitting and receiving unit to a position in the axial direction, which is specified by the count value in step S1303, are calculated. This can be done by the controller 606 which is an example of a calculating means for calculating a moving amount and moving direction of the transmitting and receiving unit.

Specifically, the difference between the count value recognized in step S1302 and the count value obtained in step S1303 is calculated and the moving amount corresponding to the count value obtained by accumulating a predetermined coefficient to the difference value is calculated. Also, the moving direction of the transmitting and receiving unit is judged according to the plus and minus of the calculated difference value.

The reason a predetermined coefficient is accumulated to the difference value is because the radial operation of the transmitting and receiving unit is started slightly before the desired position (from slightly upstream side in the axial direction motion of transmitting and receiving unit). This is because the radial operation of the transmitting and receiving unit takes a little time until the operation speed is stabilized, so that if the radial operation of the transmitting and receiving unit is started from the desired position, a situation arises in which a cross-sectional image at the desired position is imaged before the operation speed is stabilized.

Consequently, for the predetermined coefficient accumulated to the difference value, a value of 1.0 or more is used in a case in which the moving direction of the transmitting and receiving unit is opposite to the axial direction (move toward upstream side). Also, in a case in which the moving direction of the transmitting and receiving unit is the axial direction (move toward downstream side), the predetermined coefficient is less than 1.0.

Note that in the explanation above, it was assumed that a predetermined coefficient was accumulated to the difference value, but the present invention is not limited by this. It is possible for the moving amount corresponding to the difference value to be calculated and thereafter, a predetermined amount is added/subtracted according to the moving direction.

There is a return to FIG. 13. In step S1305, the control unit 606 controls the linear drive motor 131 of the linear drive apparatus 130 based on the moving amount and the moving direction which are calculated in step S1304. The control unit 606 is thus an example of a control means for moving the transmitting and receiving unit to a position corresponding to the reflected signal of the cross-sectional image disposed at the identified position appointed by the user.

As clear from the explanation above, in the imaging apparatus for diagnosis relating to this embodiment disclosed by way of example, the transmitting and receiving unit positioning button is provided and in a case in which the transmitting and receiving unit positioning button is operated (e.g., pushed down), the apparatus is configured to control the transmitting and receiving unit so as to axially move to the position of the transmitting and receiving unit at the time when the cross-sectional image corresponding to the appointed position in the axial direction on the longitudinal-sectional image was imaged.

In the imaging apparatus for diagnosis of the past, even in a case in which imaging is desired to be carried out again in the position of a disorder region, it is not possible to move the transmitting and receiving unit to the position accurately. Whereas in the imaging apparatus for diagnosis relating to this embodiment, by only appointing a position on a longitudinal-sectional image, it becomes possible for the user to move the transmitting and receiving unit automatically to a position in the axial direction corresponding to the position.

Fourth Embodiment

The third embodiment disclosed above by way of example above is such that the line data memory is arranged and the line data and the count value are correlated and stored. Consequently, the line data which are aligned in the appointed position in the axial direction on the longitudinal-sectional image are discriminated and the moving amount and the moving direction of the transmitting and receiving unit are calculated by obtaining the count value correlated with the discriminated line data.

However, the present invention is not limited in this regard, as it is possible to arrange a cross-sectional image data memory, and correlate and store a cross-sectional image and a count value. In this case, when the transmitting and receiving unit positioning button 1204 is operated or pushed down, the cross-sectional image displayed on the cross-sectional image display area 901 is discriminated and by obtaining the count value correlated with the discriminated cross-sectional image, the moving amount and the moving direction of the transmitting and receiving unit are calculated.

An alternative construction is possible in which by the user directly appointing a cross-sectional image stored in the cross-sectional image data memory, the count value correlated with the appointed cross-sectional image is obtained and the moving amount and the moving direction of the transmitting and receiving unit are calculated using the obtained count value.

In a case in which there is a constitution in which the cross-sectional image data memory is arranged in this manner, a longitudinal-sectional image is constructed based on a cross-sectional image. Specifically, a pixel value on a predetermined coordinate axis is extracted from each cross-sectional image, and it is constructed by aligning the extracted pixel value at the position corresponding to the count value correlated with each cross-sectional image and stored.

The detailed description above describes features and aspects of embodiments of an imaging apparatus for diagnosis and a control method thereof disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

The invention claimed is:

1. An imaging apparatus for diagnosis which obtains a reflected signal from inside a body lumen while a transmitting and receiving unit continuously carrying out signal transmission and reception is moved in an axial direction inside the body lumen, to generate line data used for constructing a cross-sectional image of the inside of the body lumen based on the obtained reflected signal, and which concurrently constructs multiple cross-sectional images in an axial direction inside the body lumen by using the generated line data, the imaging apparatus comprising:

a linear drive apparatus configured to move the transmitting and receiving unit in the axial direction;

a moving amount detector configured to detect information relating to a moving amount in the axial direction from a reference position of the transmitting and receiving unit, the moving amount detector being set in the linear drive apparatus and generating a different count value concurrently with each of instance of signal transmission and reception associated with generation of a different piece of line data;

storage means configured to store the line data by correlating each piece of line data with corresponding information relating to the moving amount in the axial direction from the reference position of the transmitting and receiving unit, the information relating to the moving amount being based on the count value generated concurrently with the instance of signal transmission and reception associated with generation of the piece of line data to be correlated with the information related to the moving amount;

construction means configured to construct a longitudinal-sectional image with respect to the multiple cross-sectional images constructed in the axial direction by extracting, from the storage means, line data corresponding to coordinate positions in the respective cross-sectional images from among the multiple line data used for constructing the respective cross-sectional images, concurrently, by obtaining information relating to a moving amount of the transmitting and receiving unit in the axial direction from the reference position, which is received when the extracted line data is generated, and by aligning the extracted line data at a position in response to the information relating to the obtained moving amount;

display means configured to display the constructed longitudinal-sectional image;

an indicator displayed on the display means;

reconstruction means configured to reconstruct the cross-sectional image by identifying the line data by being correlated with the information of a position appointed by the indicator on the displayed longitudinal-sectional image, concurrently, by reading out, from the storage means, line data with which there is correlated the same information as the information relating to the moving amount in the axial direction stored by being correlated with the line data, and by using the read out line data; and the display means is configured to display the reconstructed cross-sectional image together with the longitudinal-sectional image.

2. The imaging apparatus for diagnosis according to claim 1, wherein the display means is configured to display two or more indicators which are configured to appoint two or more positions, and the reconstruction means is configured to construct two or more cross-sectional images by identifying the line data disposed at the appointed positions.

3. The imaging apparatus for diagnosis according to claim 2, wherein:

the reconstruction means is configured to identify the line data disposed at the appointed positions and concurrently, calculate a distance between the appointed two points by reading out information relating to the moving amounts in the axial direction, which is stored in a manner correlated with the respective line data; and the display means, further, is configured to display the distance between the two points calculated by the reconstruction means.

4. The imaging apparatus for diagnosis according to claim 1, wherein:

the indicator is configured to appoint a position in the axial direction; and the linear drive apparatus is configured to automatically move the transmitting and receiving unit to the position appointed by the indicator.

5. The imaging apparatus for diagnosis according to claim 4, further comprising a display for successively displaying the multiple cross-sectional images as well as a longitudinal-sectional image of the inside of the body lumen.

6. The imaging apparatus for diagnosis according to claim 1, wherein the storage means is configured to store the reference position as a position between maximum forward position and maximum backward position of the transmitting and receiving unit.

7. The imaging apparatus for diagnosis according to claim 1, wherein the count value is of a pulse signal.

* * * * *